United States Patent
Moraes et al.

(10) Patent No.: US 12,296,000 B2
(45) Date of Patent: May 13, 2025

(54) SLAM POLYNUCLEOTIDES AND POLYPEPTIDES AND USES THEREOF

(71) Applicant: ENGINEERED ANTIGENS INC., Calgary (CA)

(72) Inventors: Trevor F. Moraes, Toronto (CA); Christine Chieh-Lin Lai, Toronto (CA); Yogesh Hooda, Toronto (CA); Andrew Judd, Mississauga (CA); Anthony B. Schryvers, Calgary (CA); Scott D. Gray-Owen, Oakville (CA)

(73) Assignee: Engineered Antigens Inc., Calgary (CA)

( * ) Notice: Subject to any disclaimer, the term of this patent is extended or adjusted under 35 U.S.C. 154(b) by 0 days.

(21) Appl. No.: 18/544,698

(22) Filed: Dec. 19, 2023

(65) Prior Publication Data

US 2024/0181029 A1    Jun. 6, 2024

Related U.S. Application Data

(63) Continuation of application No. 17/405,620, filed on Aug. 18, 2021, now Pat. No. 11,872,275, which is a continuation of application No. 16/077,112, filed as application No. PCT/CA2017/050160 on Feb. 10, 2017, now Pat. No. 11,123,418.

(60) Provisional application No. 62/293,491, filed on Feb. 10, 2016.

(51) Int. Cl.

| | |
|---|---|
| *A61K 39/02* | (2006.01) |
| *A61K 39/095* | (2006.01) |
| *C07K 14/195* | (2006.01) |
| *C07K 14/22* | (2006.01) |
| *C12P 21/06* | (2006.01) |
| *A61K 39/00* | (2006.01) |

(52) U.S. Cl.
CPC ............ *A61K 39/095* (2013.01); *A61K 39/02* (2013.01); *C07K 14/195* (2013.01); *C07K 14/22* (2013.01); *A61K 2039/522* (2013.01); *A61K 2039/523* (2013.01); *Y02A 50/30* (2018.01)

(58) Field of Classification Search
None
See application file for complete search history.

(56) References Cited

FOREIGN PATENT DOCUMENTS

| | | |
|---|---|---|
| CA | 2931685 A1 | 6/2015 |
| WO | 1998/056901 A2 | 12/1998 |
| WO | 2009/114485 A2 | 9/2000 |
| WO | 2006/027584 A2 | 3/2006 |

OTHER PUBLICATIONS

Notice of Reasons for Rejection for JP Application No. 2018-543163 dated Jan. 5, 2022.
English Translation of Notice of Reasons for Rejection for JP Application No. 2018-543163 dated Jan. 5, 2022.
Calmettes, C. et al., "Structural aspects of bacterial outer membrane protein assembly", Advances in Experimental Medicine and Biology, 2015, vol. 883, p. 255-70.
Danve, B. et al. "Transferrin-binding proteins isolated from Neisseria meningitidis elicit protective and bacterial antibodies in laboratory animals", Vaccine, 1993, vol. 11(12), p. 1214-1220.
Database UniParc [Online] uniprot; Apr. 6, 2006, Database accession No. UPI00025C57E9.
Feavers, I.M. et al., "Meningococcal protein antigens and vaccines", Vaccine, 2009, vol. 27S, p. B42-B50.
Hooda, Y. et al., "Slam is an outer membrane protein that is required for the surface display of lipidated virulence factors in Neisseria", Nature Microbiology, ePub. Feb. 29, 2016, vol. 1, p. 16009.
Lauber, F. et al., "Identification of a new lipoprotein export signal in gram-negative bacteria", mBio, Oct. 25, 2016, vol. 7(5), p. e01232-16.
Mikayama et al., Proc. Natl. Acad. Sci. USA, vol. 90, Nov. 1993.
Pajon, R. et al., "A nature outer membrane vesicle vaccine confers protection against meningococcal colonization in human CEACAM1 transgenic mice", Vaccine, Mar. 10, 2015, vol. 33(11), p. 1317-1323.
Salverda, M.L.M., et al., "Surface display of a borrelial lipoprotein on meningococcal outer membrane vesicles", Vaccine, ePub: Jan. 19, 2016, vol. 34, p. 1025-1033.
Yan et al. Fly (2018), 12 (3-4), 191-198.
Zhong et al., American Soc. Micreobio. 2013, 33(6):1223-1232.

*Primary Examiner* — Jennifer E Graser
(74) *Attorney, Agent, or Firm* — SMART & BIGGAR LP; Micheline Gravelle

(57) ABSTRACT

Novel methods for exporting target proteins from the cytosol to the extracellular surface of bacterial cells are provided. The methods are useful in that they permit the preparation of vaccines for the prevention of bacterial infectious diseases.

16 Claims, 15 Drawing Sheets

Figure 1:
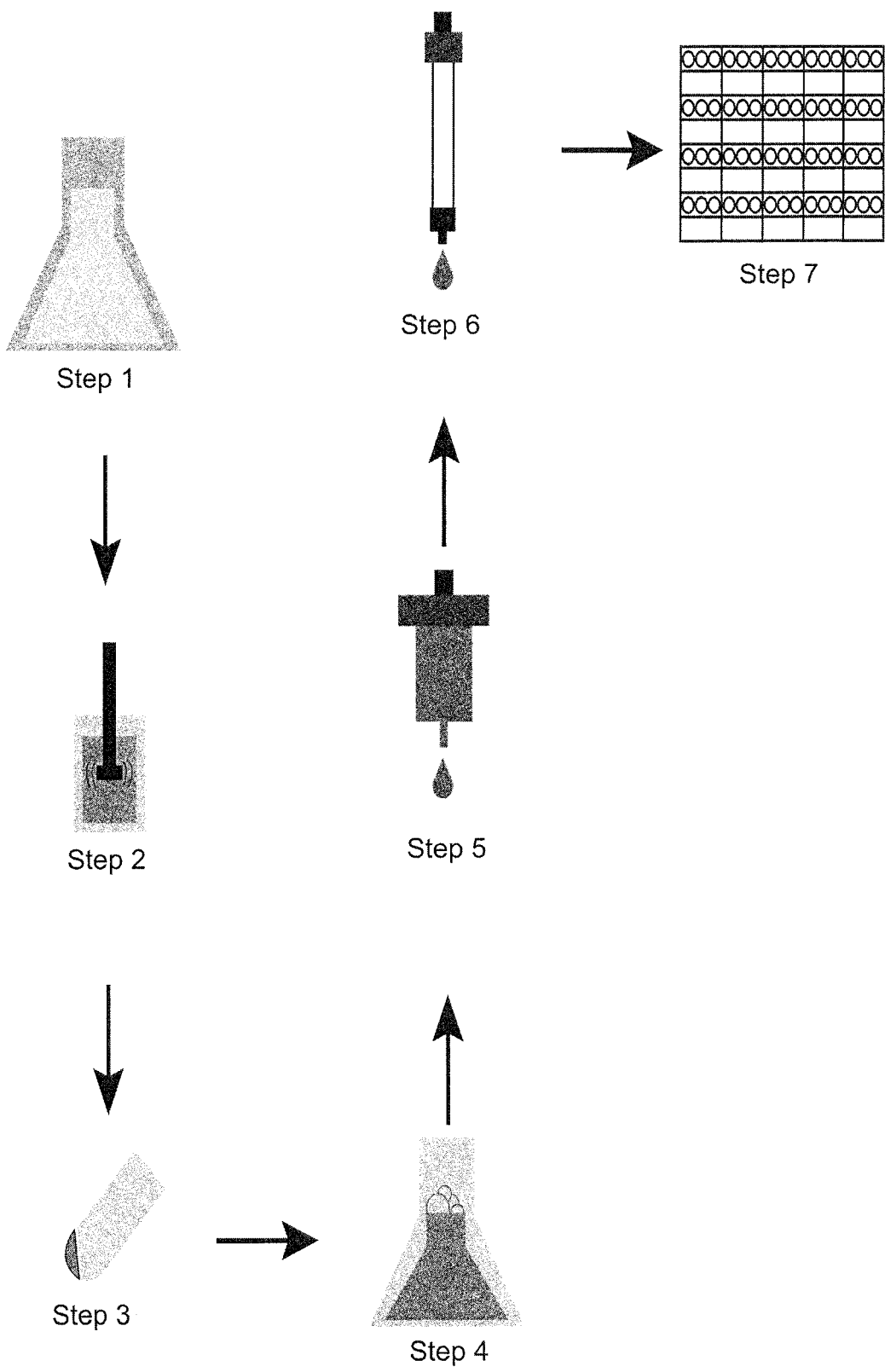

Specification includes a Sequence Listing.

Figures 2A-C

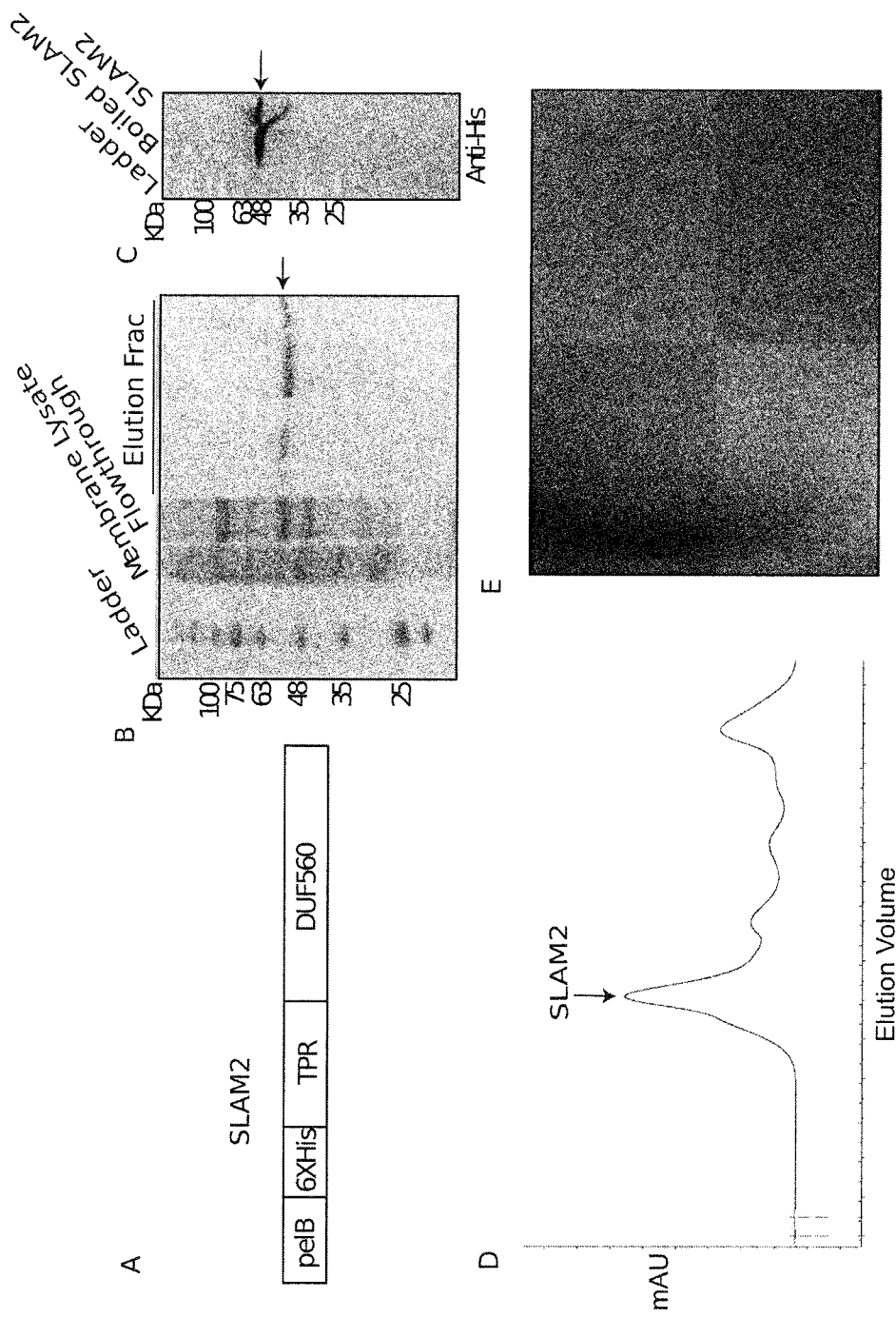
Figures 4A-E

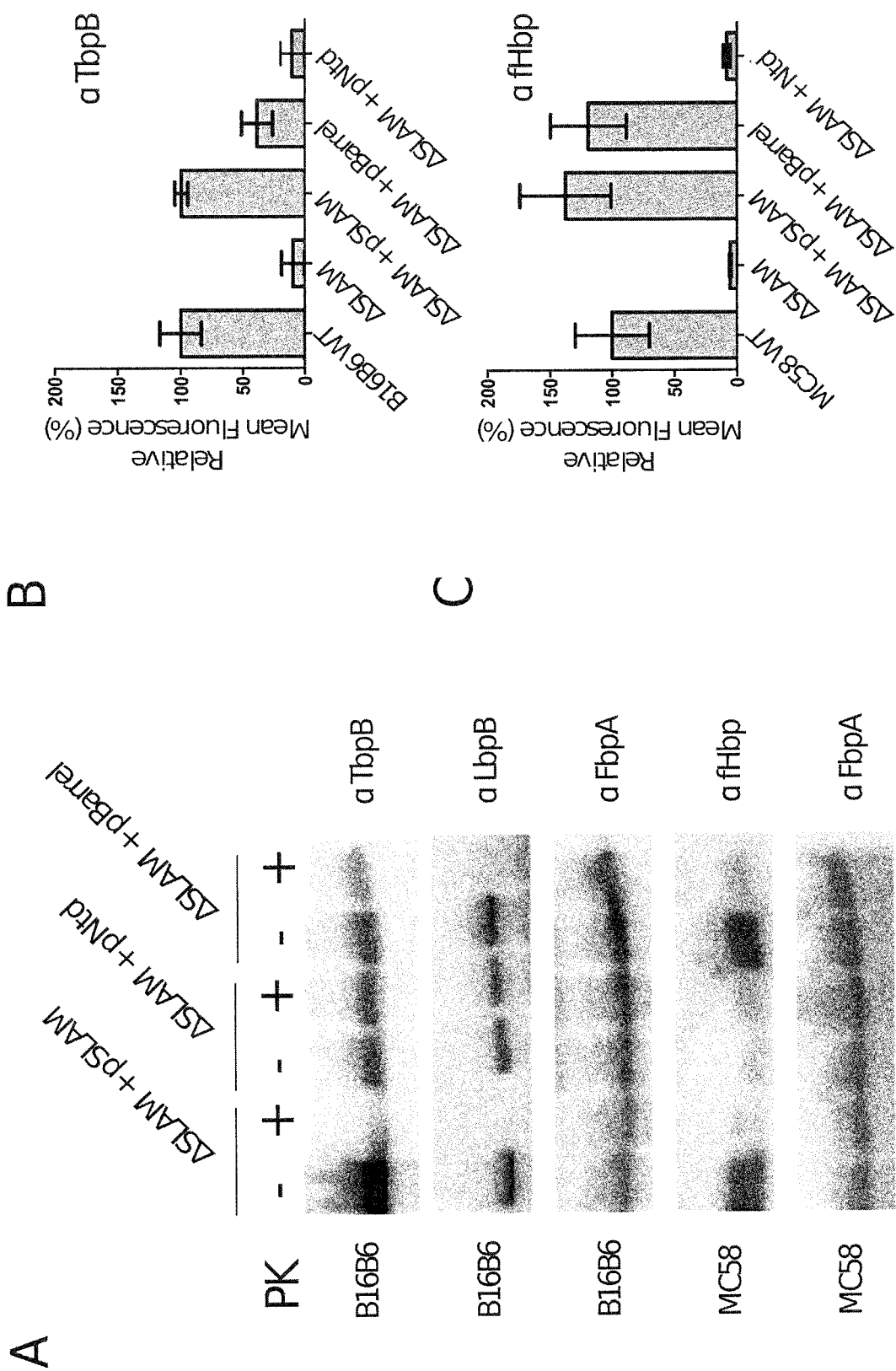
Figures 5A-C

A
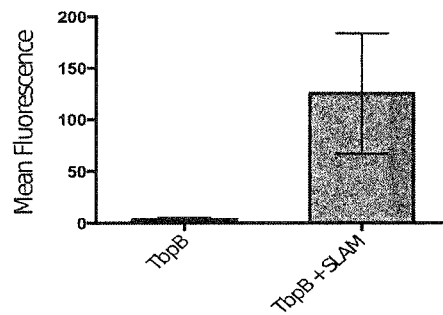
B
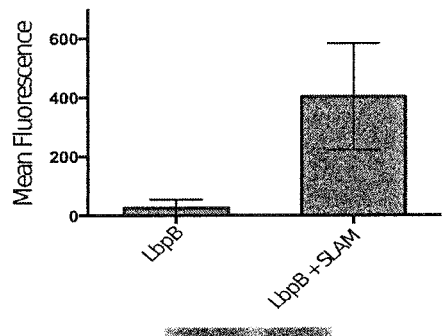
C
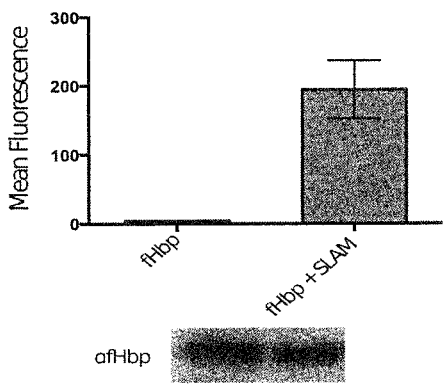
Figures 6A-C

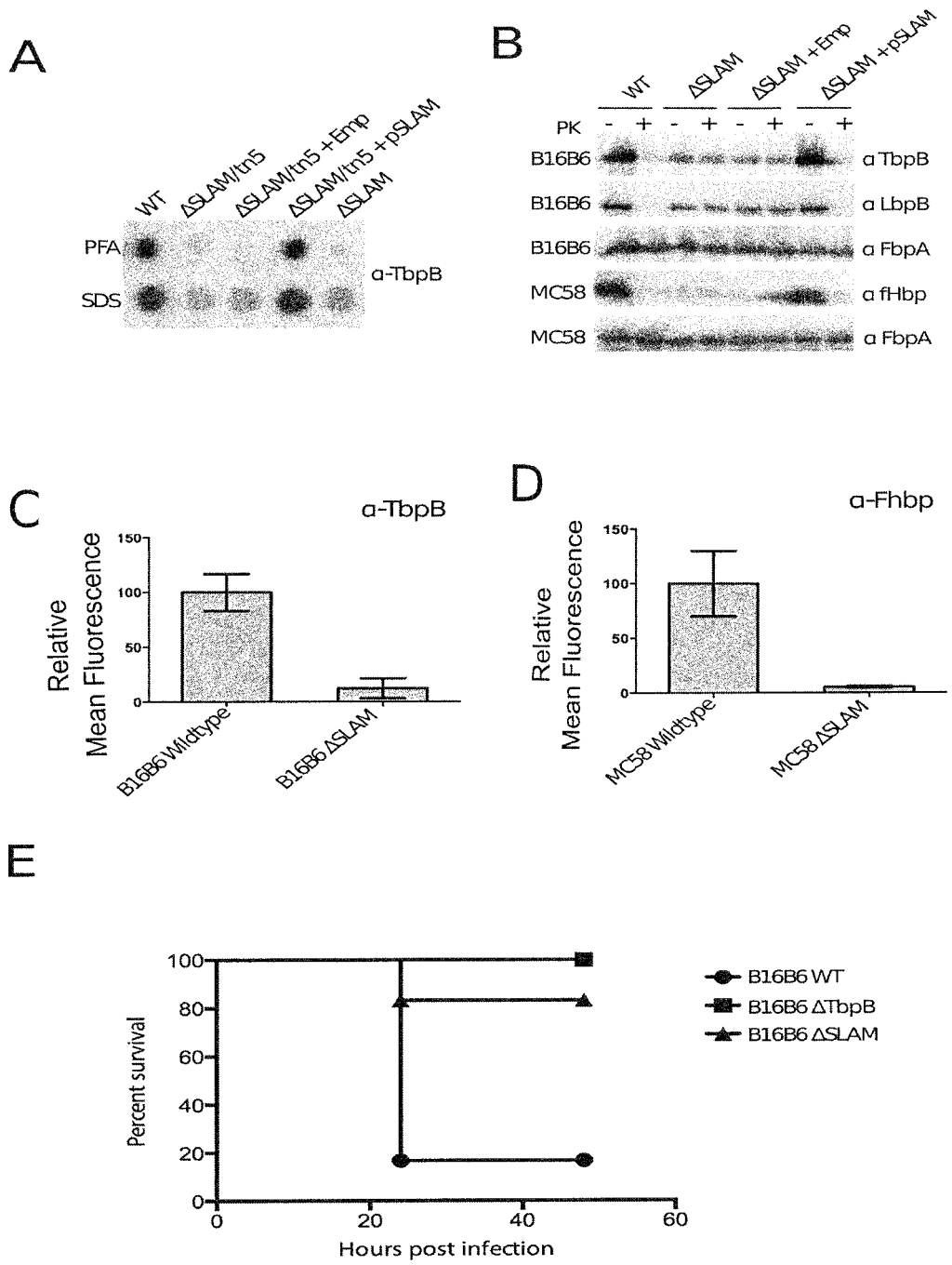
Figures 7A-E

Proteobacteria

```
├── Alpha-proteobacteria ─┬── Sphingomonadaceae ──── Sphingomonas melonis (1)
│                         │                          Novosphingobium resinovorum (1)
│                         │                          Sphingobium japonicum (1)
│                         ├── Rhizobiales ────────── Martelella mediterranea (2)
│                         │                          Nitratireductor indicus (1)
│                         └── Rhodobacteraceae ───── Sulfitobacter pontiacus (2)
│                                                    Oceanicola batsensis (1)
│
├── Beta-proteobacteria ──┬── Neisseriaceae ─┬── Neisseria ─── Neisseria meningitidis (2)
│                         │                  │                 Neisseria gonorrhoeae (3)
│                         │                  │                 Neisseria lactamica (4)
│                         │                  │                 Neisseria elongata (2)
│                         │                  ├── Kingella ──── Kingella kingae (4)
│                         │                  │                 Kingella denitrificans (5)
│                         │                  └── Eikenella corrodens (2)
│                         ├── Burkholderiales ─── Alcaligenes faecalis (1)
│                         │                       Achromobacter xylosoxidans (1)
│                         │                       Taylorella equigenitalis (2)
│                         └── Rhodocyclaceae ───── Thauera linaloolentis (2)
│
├── Gamma-proteobacteria ─┬── Pasteurellaceae ─┬── Pasteurella ─── Pasteurella multocida (1)
│                         │                    ├── Haemophilus ─── Haemophilus influenzae (2)
│                         │                    │                   Haemophilus parainfluenzae (2)
│                         │                    │                   Haemophilus parasuis (3)
│                         │                    ├── Mannheimia ──── Mannheimia haemolytica (4)
│                         │                    │                   Mannheimia varigena (2)
│                         │                    ├── Aggregatibacter ─── Aggregatibacter actinomycetemcomitans (1)
│                         │                    ├── Actinobacillus ─── Actinobacillus pleuropneumoniae (3)
│                         │                    │                      Actinobacillus suis (3)
│                         │                    └─── Bibersteinia trehalosi (5)
│                         │                         Histophilus somni (2)
│                         │                         Gallibacterium anatis (3)
│                         ├── Pseudomonadales ─┬── Acinetobacter ── Acinetobacter baumannii (1)
│                         │                    │                    Acinetobacter calcoaceticus (1)
│                         │                    ├── Pseudomonas ──── Pseudomonas fluorescens (1)
│                         │                    │                    Pseudomonas putida (2)
│                         │                    │                    Pseudomonas aeruginosa strain PA1 (1)
│                         │                    └── Psychrobacter phenylpyruvicus (1)
│                         │                        Moraxella catarrhalis (2)
│                         ├── Enterobacteriaceae ─┬── Xenorhabdus ── Xenorhabdus nematophila (2)
│                         │                       │                  Xenorhabdus bovienii (1)
│                         │                       ├── Providencia ── Providencia alcalifaciens (1)
│                         │                       │                  Providencia rettgeri (2)
│                         │                       └── Proteus mirabilis (1)
│                         │                           Photorhabdus temperata (1)
│                         │                           Escherichia coli strain UMEA (1)
│                         │                           Salmonella enterica subsp. arizonae & diarizonae (1)
│                         │                           Morganella morganii (1)
│                         ├── Vibrionaceae ──────── Vibrio nigripulchritudo (1)
│                         │                         Vibrio cholerae strains: O37, MZO-3, PS15 (1)
│                         ├── Xanthomonadaceae ──── Stenotrophomonas maltophilia (1)
│                         │                         Stenotrophomonas sp. SKA14 (1)
│                         ├── Cardiobacteriaceae ── Cardiobacterium valvarum (2)
│                         └── Methylophaga ──────── Methylophaga lonarensis (1)
│
└── Delta-proteobacteria ── Desulfovibrionaceae ──── Desulfurivibrio alkaliphilus (1)
```

Figure 8

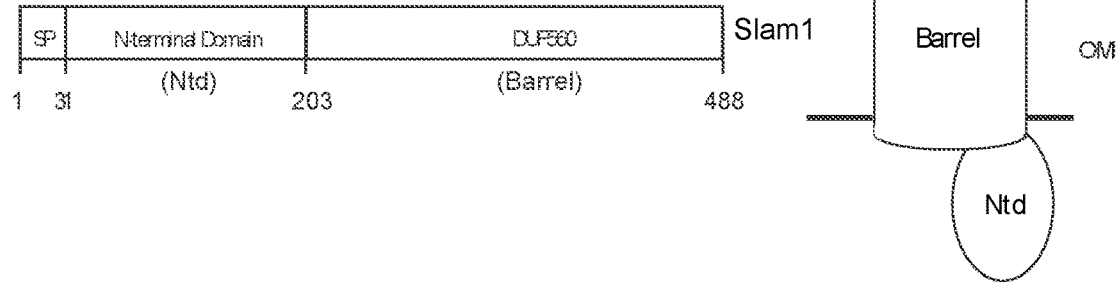
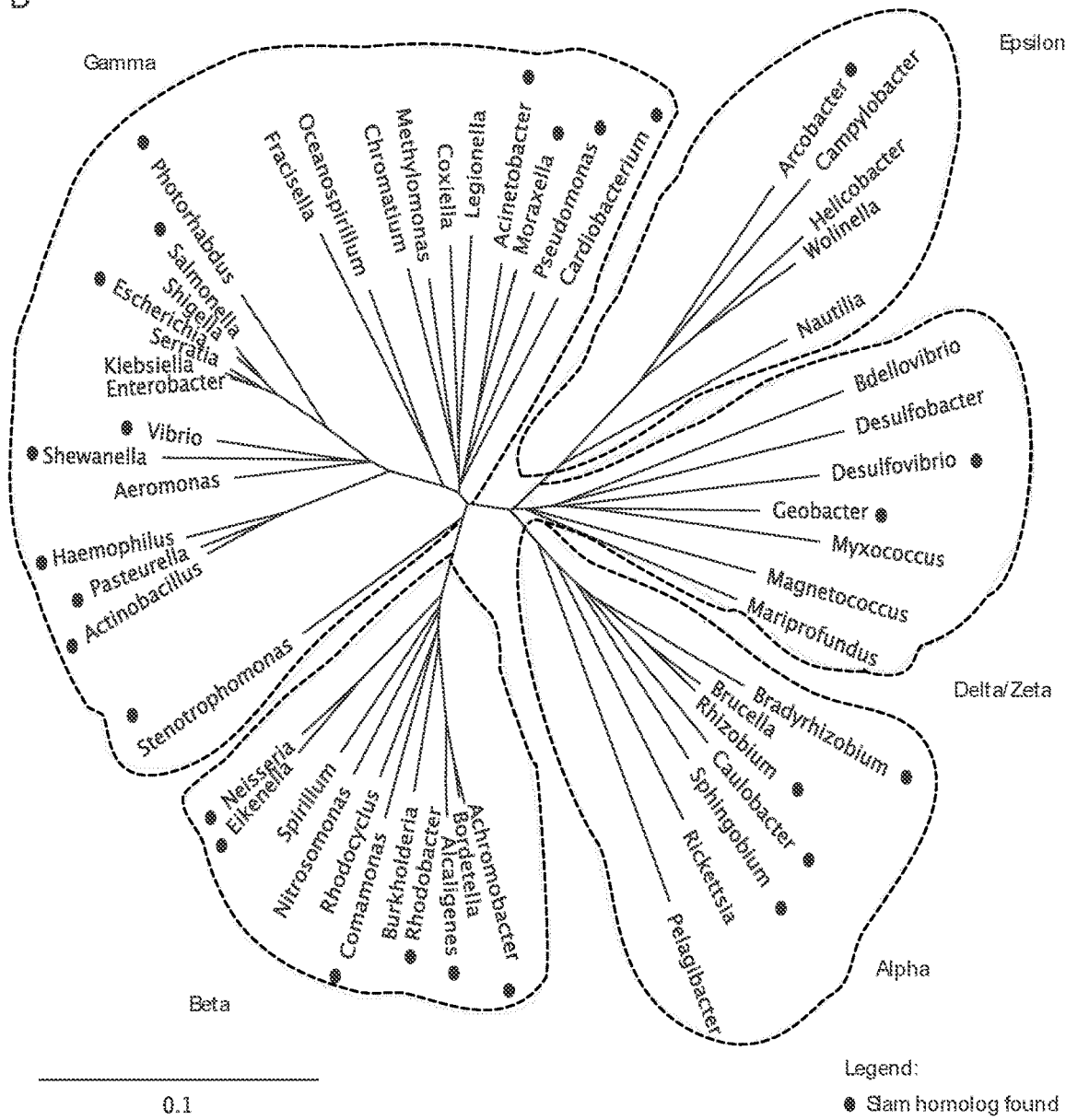
Figures 9A-B

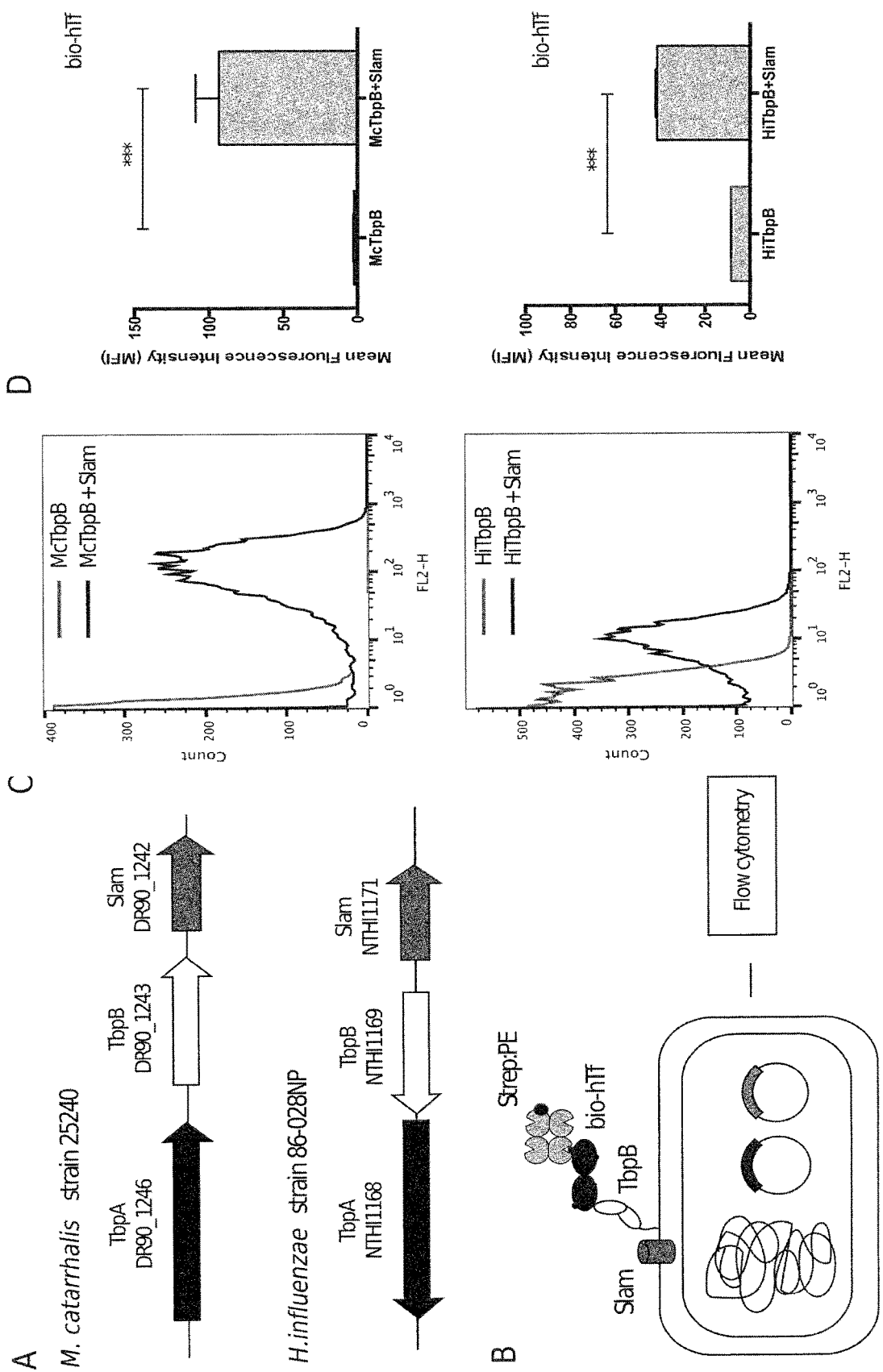
Figures 10A-D

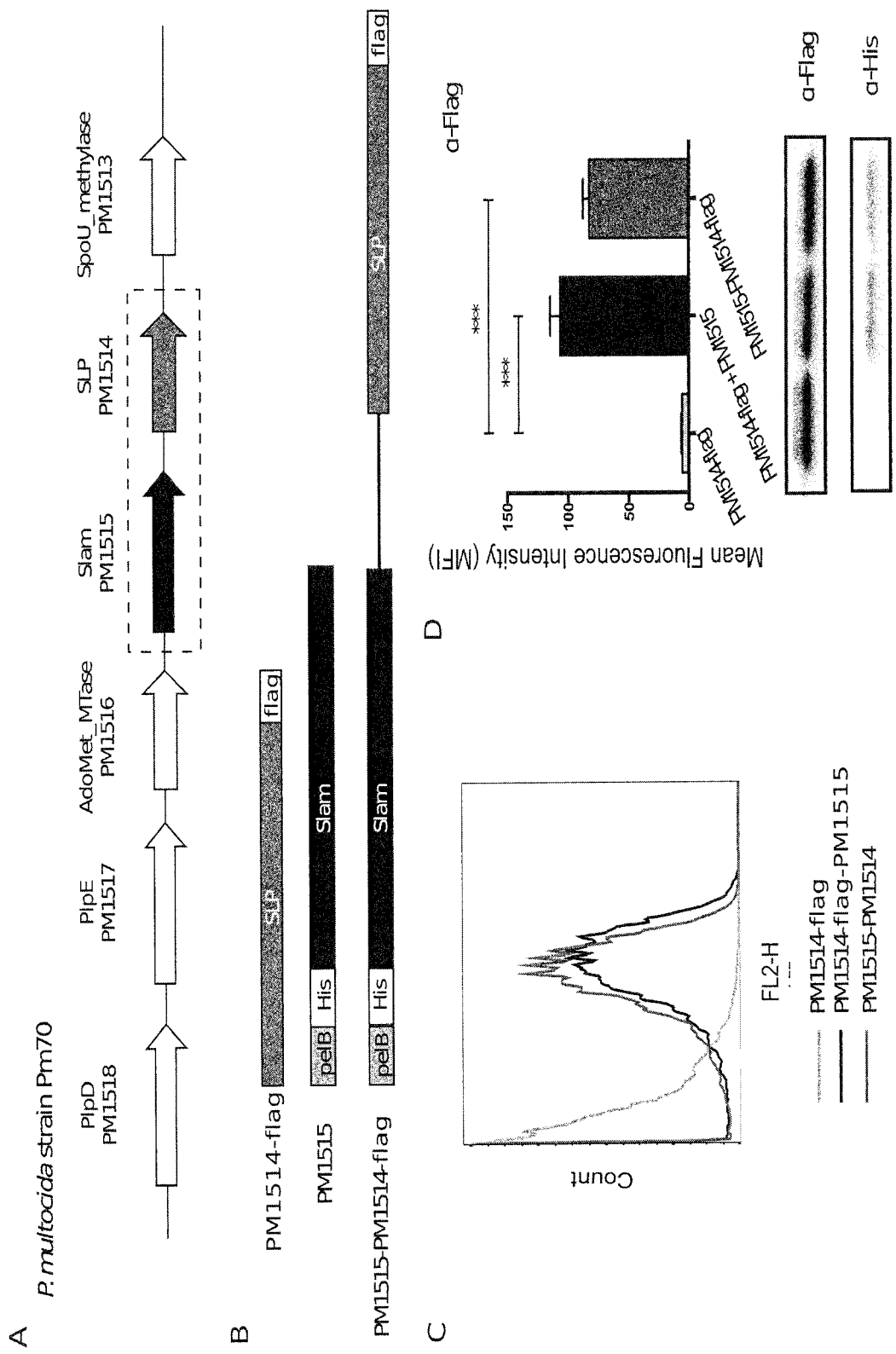
Figures 11A-D

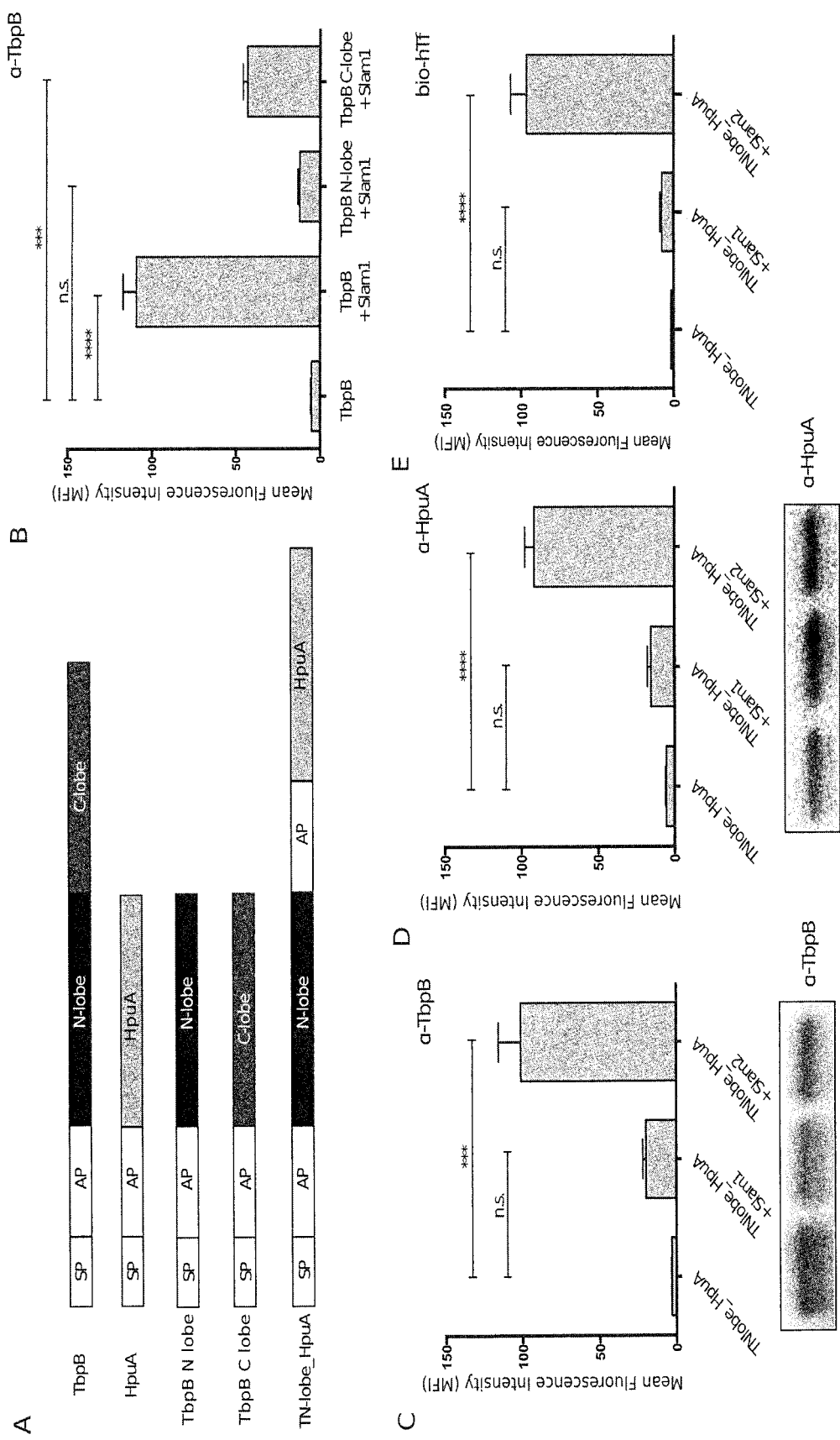
Figures 12A-E

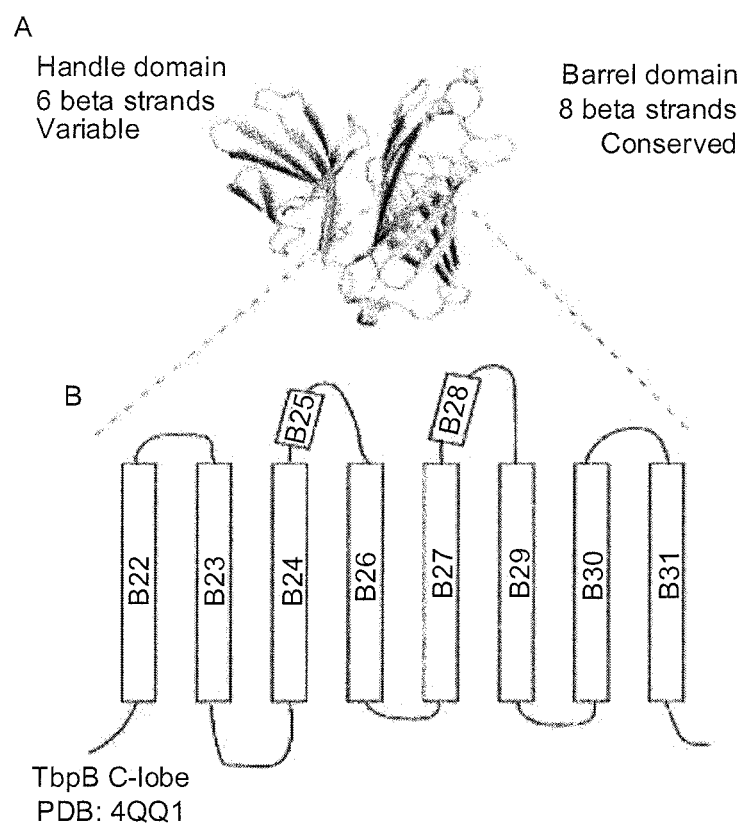
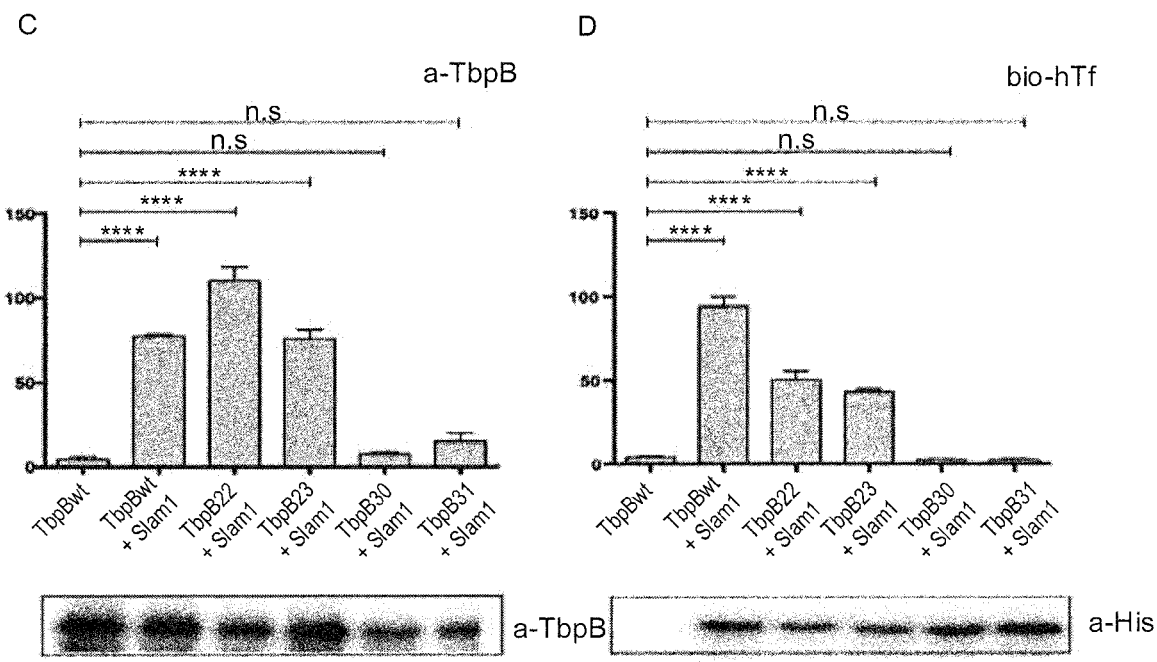
Figures 13A-D

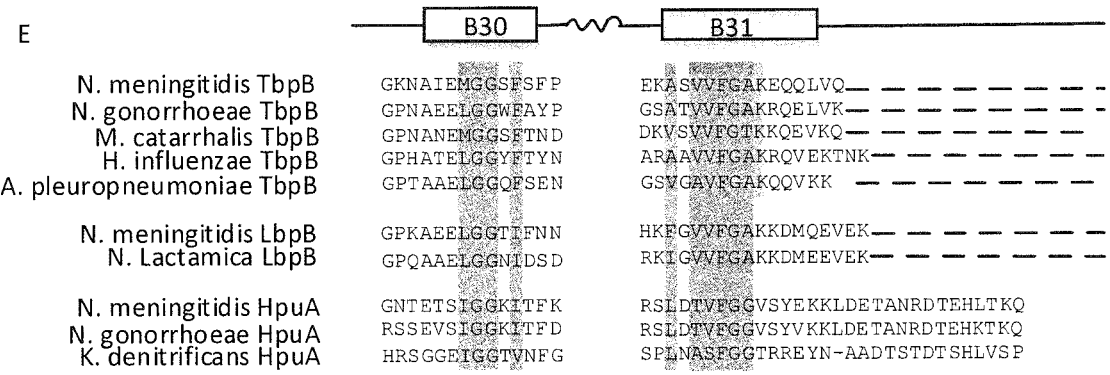
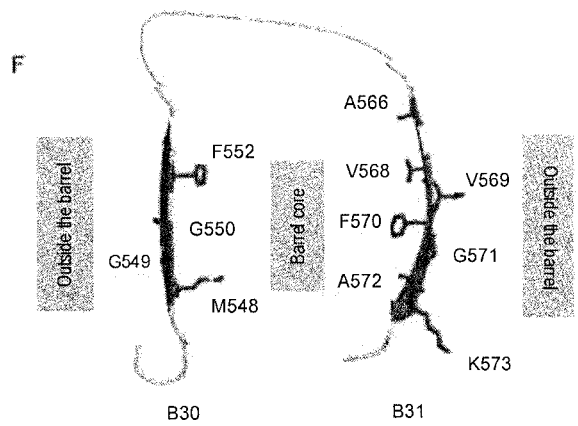
Figures 13E-F

A
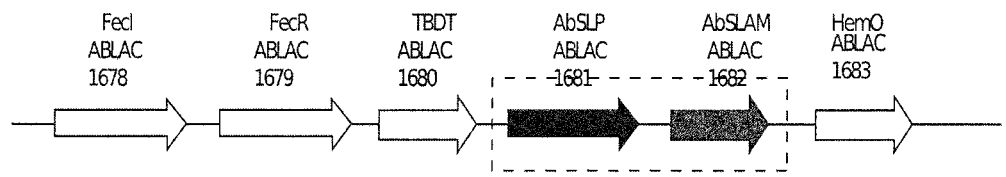
B
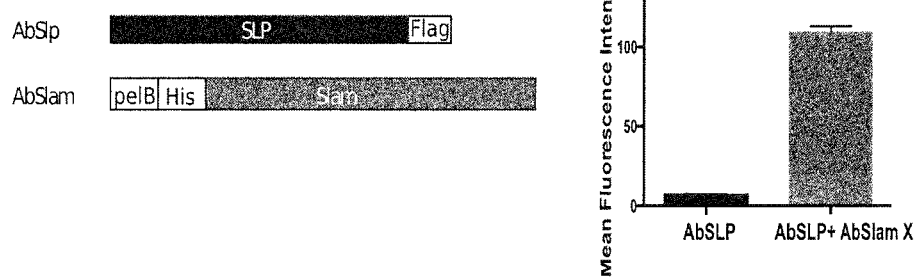
C
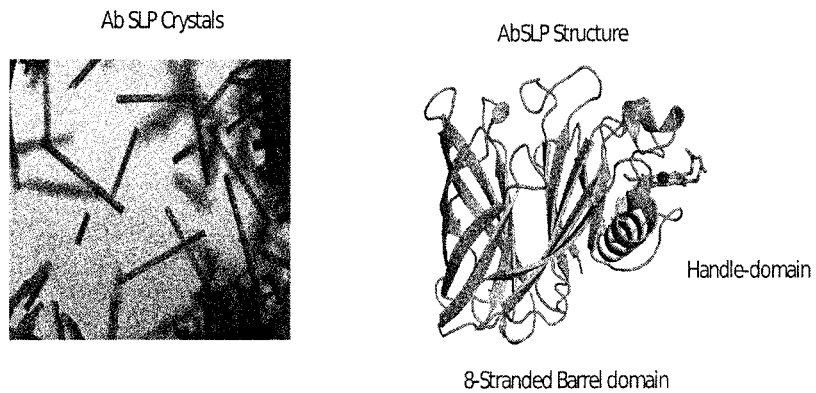
D
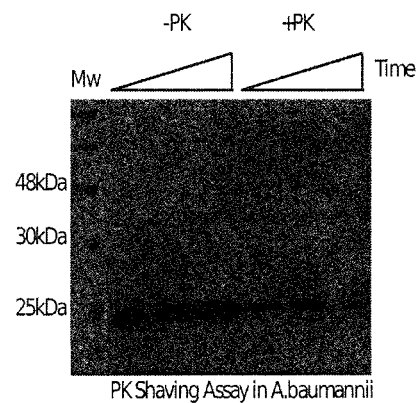
Figures 14A-D

SLAM POLYNUCLEOTIDES AND POLYPEPTIDES AND USES THEREOF

CROSS-REFERENCE TO RELATED APPLICATION

This application is a continuation of U.S. patent application Ser. No. 17/405,620 (now allowed), which is a continuation of U.S. patent application Ser. No. 16/077,112 (now issued as U.S. Pat. No. 11,123,418), which is a national phase entry application of Patent Cooperation Treaty Application No. PCT/CA2017/050160 filed Feb. 10, 2017 (which designates the U.S.), which claims the benefit of U.S. Provisional Patent Application No. 62/293,491 filed Feb. 10, 2016. The entire contents of patent application Ser. Nos. 17/405,620, 16/077,112, PCT/CA2017/050160, and 62/293,491 and are hereby incorporated by reference in their entirety.

INCORPORATION OF SEQUENCE LISTING

A computer readable form of the Sequence Listing "21806-P47204US04_SequenceListing.xml" (2,271,235 bytes), submitted via Patent Center and created on Dec. 15, 2023, is herein incorporated by reference.

FIELD OF THE DISCLOSURE

The present disclosure relates to a class of polypeptides known as surface lipoprotein assembly modulator polypeptides, or SLAM polypeptides, and polynucleotides encoding SLAM polypeptides, and substrates thereof, surface lipoproteins (SLPs). The SLAM polypeptides are obtainable from Gram-negative bacterial species. The SLAM polypeptides and polynucleotides are useful in the prevention and treatment of infectious diseases caused by pathogenic bacterial species, including, for example, bacterial species belonging to the genus *Neisseria*.

BACKGROUND OF THE DISCLOSURE

The following paragraphs are intended to introduce the reader to the more detailed description that follows and not to define or limit the claimed subject matter of the present disclosure.

Pathogenic bacterial species, including bacterial species belonging to the genus *Neisseria* are causative agents of large epidemic diseases. Thus, for example meningitis is caused by *Neisseria meningitidis*, and gonorrhea, is caused by *Neisseria gonorrhoeae*. The World Health Organization (WHO) reported over 88,000 suspected cases of meningitis in 2009 in 14 countries within the sub-Saharan Africa of the so called "meningitis belt", of which more than 5,300 resulted in death (WHO Fact Sheet No 141, November 2012). Sporadic meningitis outbreaks occur elsewhere, including in North America, as well. Gonorrhea has been estimated to affect over 100 million people worldwide with 820,000 new cases being reported in the US alone, on an annual basis. While antibiotics, such as ampicillin, tetracycline and quinolones, offer treatment options against *Neisseria* infections, resistance to these antibiotics is an increasingly significant concern. Vaccines offering protection against *Neisseria* infections have been developed, however there is an ongoing need for additional vaccines, as depending on the serogroup, efficacy of the vaccines varies. Thus, for example, the efficacy of a vaccine known as 4CMenB, a four-component vaccine against *Neisseria meningitidis* serogroup B, remains to be established and paediatric use in Canada is only recommended for individuals at the highest risk of invasive meningococcal disease (Robinson J L, Paediatric Child Health, 2014 19(2): 91-94). There are still no vaccines available for *N. gonorrhoeae*.

Therefore there is a need in the art to develop further treatment and prevention options against infections caused by pathogenic *Neisseria* species and other pathogenic bacterial species.

SUMMARY OF THE DISCLOSURE

In one aspect, the present disclosure relates to a class of polypeptides known as surface lipoprotein assembly modulator (SLAM) polypeptides.

In another aspect, the present disclosure relates to the production of SLAM polypeptides in host cells, including pathogenic or non-pathogenic bacterial cells.

In another aspect, the present disclosure relates to the transport of certain target proteins within a cell from the cytosol to the extracellular surface area of the cell.

Accordingly, in one aspect, the present disclosure provides, in at least one embodiment, a method of effecting transport of a target protein from the cytosol to the extracellular surface of a host cell comprising the target protein, the method comprising:
 (a) providing a chimeric polynucleotide comprising as operably linked components:
  (i) a polynucleotide capable of controlling expression in the host cell; and
  (ii) a polynucleotide encoding a SLAM polypeptide; and
 (b) introducing the chimeric polynucleotide in the host cell and growing the host cell to produce the SLAM polypeptide, thereby effecting transport of the target protein from the cytosol to the extracellular surface of the host cell.

In some embodiments, the host cell is a Gram-negative bacterial cell.

In some embodiments, the host cell is a pathogenic bacterial cell.

In some embodiments, the host cell is a cell selected from bacterial cells belonging to the genus *Neisseria, Klebsiella, Moraxella, Mannheimia, Actinobacillus, Haemophilus, Pasteurella, Acinetobacter, Escherichia* or *Vibrio*.

In some embodiments, the host cell is selected from bacterial cells belonging to the species *Neisseria meningitidis, Neisseria gonorrhoeae, Neisseria lactamica, Neisseria cincera, Klebsiella denitrificans, Moraxella catarrhalis, Mannheimia haemolytica, Actinobacillus pleuropneomoniae, Haemophilus somni, Haemophilus influenzae, Pasteurella multocida, Acinetobacter baumannii, Escherichia coli* or *Vibrio cholera*.

In some embodiments, the SLAM polypeptide is not naturally present in the host cell.

In some embodiments, the target protein is naturally present in the host cell.

In some embodiments, the target protein is not naturally present in the host cell.

In some embodiments, the target protein is non-covalently associated to the SLAM polypeptide.

In some embodiments, the target protein is covalently linked to the SLAM polypeptide.

In some embodiments, the target protein is an immunogen capable of eliciting an immune response in a host organism.

In some embodiments, the target protein is an immunogenic polypeptide, or an immunogenic portion thereof, that is naturally displayed on the exterior surface of a pathogenic microorganism.

In some embodiments, the target protein is a surface lipoprotein (SLP).

In some embodiments, the surface lipoprotein (SLP) comprises or consists of a sequence selected from one of the even-numbered SEQ ID NOs: SEQ ID NO: 696 to SEQ ID NO: 1082; SEQ ID NO: 1094; SEQ ID NO: 1100; even-numbered SEQ ID NOs: 1116 to SEQ ID NO: 1168; and SEQ ID NO; 1178 set forth herein.

In some embodiments, the surface lipoprotein is selected from a transferrin binding protein B (TbpB), a hemoglobin-haptoglobin binding protein A (HpuA), a Factor H binding protein (fHbp), and a lactoferrin binding protein (LbpB).

In some embodiments, the transferrin binding protein B (TbpB) comprises or consists of a sequence selected from SEQ ID NO: 806, SEQ ID NO: 828, SEQ ID NO: 868, SEQ ID NO: 1094, and one of the even-numbered SEQ ID NOs: SEQ ID NO: 1148 to SEQ ID NO: 1168 set forth herein; the hemoglobin-haptoglobin binding protein A (HpuA) comprises or consists of a sequence selected from one of SEQ ID NO: 850, SEQ ID NO: 924, SEQ ID NO: 932, or SEQ ID NO: 1110 set forth herein, the Factor H binding protein (fHbp) comprises or consists of a sequence selected from one of the even-numbered SEQ ID NOs: SEQ ID NO: 1116 to SEQ ID NO:1136 set forth herein, and the lactoferrin binding protein (LbpB) comprises or consists of a sequence selected from SEQ ID NO: 870 or one of the even-numbered SEQ ID NOs: SEQ ID NO: 1138 to SEQ ID NO: 1146 set forth herein.

In some embodiments, the polynucleotide encoding the SLAM polypeptide comprises or consists of a sequence selected from one of the odd-numbered SEQ ID NOs: SEQ ID NO: 1 to SEQ ID NO: 693 set forth herein.

In some embodiments, the target protein comprises or consists of a sequence selected from one of the even-numbered SEQ ID NOs: SEQ ID NO: 696 to SEQ ID NO: 1082, SEQ ID NO: 1094; SEQ ID NO: 1100; even-numbered SEQ ID NOS: 1116 to SEQ ID NO: 1168; and SEQ ID NO; 1178.

In another aspect, the present disclosure provides, in at least one embodiment, a method of effecting transport of a target protein from the cytosol to the extracellular surface of a host cell comprising:
  (a) selecting a host cell comprising a target protein naturally present in the cell;
  (b) providing a chimeric polynucleotide comprising as operably linked components:
    (i) a polynucleotide capable of controlling expression in the host cell; and
    (ii) a polynucleotide encoding a SLAM polypeptide; and
  (c) introducing the chimeric nucleic acid sequence in the host cell and growing the host cell to produce the SLAM polypeptide and effect transport of the target protein from the cytosol to the extracellular surface.

In another aspect, the present disclosure provides, in at least one embodiment, a method of effecting transport of a target protein from the cytosol to the extracellular surface of a host cell comprising:
  (a) providing a chimeric polynucleotide comprising as operably linked components:
    (i) a polynucleotide capable of controlling expression in the host cell;
    (ii) a polynucleotide encoding a SLAM polypeptide; and
    (iii) a polynucleotide encoding a target protein; and
  (b) introducing the chimeric nucleic acid sequence in the host cell and growing the host cell to produce the SLAM polypeptide and effect transport of the target protein from the cytosol to the extracellular surface.

In another aspect, the present disclosure provides a method of effecting transport of a target protein from the cytosol to the extracellular surface of a host cell comprising:
  (a) providing a first chimeric polynucleotide comprising as operably linked components:
    (i) a polynucleotide capable of controlling expression in the host cell; and
    (ii) a polynucleotide encoding a SLAM polypeptide; and
  (b) providing a second chimeric polynucleotide comprising as operably linked components:
    (i) a polynucleotide capable of controlling expression in the host cell; and
    (ii) a polynucleotide encoding a target protein; and
  (c) introducing the first and second chimeric polynucleotide in the host cell and growing the host cell to produce the SLAM polypeptide and the target protein and effect transport of the target protein from the cytosol to the extracellular surface.

In another aspect, the present disclosure relates to novel polynucleotides encoding SLAM polypeptides. Accordingly, the present disclosure provides, in at least one embodiment, a polynucleotide comprising or consisting of SEQ ID NO: 1183.

In some embodiments, the polynucleotide encoding a SLAM polypeptide wherein the SLAM polynucleotide has been modified to facilitate expression of a SLAM polypeptide in a host cell.

In some embodiments, the polynucleotide encoding the SLAM polypeptide has been codon-optimized.

In some embodiments, the codon-optimized polynucleotide comprises or consists of a sequence set forth in SEQ ID NO: 1113.

In some embodiments, the polynucleotide encoding the polynucleotide SLAM polypeptide additionally comprises a signal sequence.

In another aspect, the present disclosure relates to novel polypeptides. Accordingly the present disclosure provides, in at least one embodiment, a polypeptide comprising or consisting of SEQ ID NO: 1184.

In another aspect, the present disclosure provides, in at least one embodiment, a method of preparing a vaccine comprising:
  (a) selecting a host cell capable of producing an immunogen;
  (b) providing a chimeric polynucleotide comprising as operably linked components:
    (i) a polynucleotide capable of controlling expression in the host cell; and
    (ii) a polynucleotide encoding a SLAM polypeptide; and
  (c) introducing the chimeric nucleic acid sequence in the host cell and growing the host cell to produce the SLAM polypeptide and the immunogen;
  (d) attenuating the host cell to prepare an attenuated host cell; and
  (e) preparing a vaccine formulation using the attenuated host cell.

In another aspect, the present disclosure provides, in at least one embodiment, a method of preparing a vaccine comprising:
(a) providing a first chimeric polynucleotide comprising as operably linked components:
  (i) a polynucleotide capable of controlling expression in the host cell;
  (ii) a polynucleotide encoding a SLAM polypeptide; and
(b) providing a second chimeric polynucleotide comprising as operably linked components:
  (i) a polynucleotide capable of controlling expression in the host cell; and
  (ii) a polynucleotide encoding a target protein; and
(c) introducing the first and second chimeric polynucleotide in the host cell and growing the host cell to produce the SLAM polypeptide and the target protein; and
(d) preparing a vaccine formulation using the cells of (c).

In another aspect, the present disclosure provides, in at least one embodiment, a method of preparing a vaccine comprising:
(a) providing a chimeric polynucleotide comprising as operably linked components:
  (i) a polynucleotide capable of controlling expression in the host cell;
  (ii) a polynucleotide encoding a SLAM polypeptide; and
  (iii) a polynucleotide encoding a target protein; and
(b) introducing the chimeric polynucleotide in the host cell and growing the host cell to produce the SLAM polypeptide and the target protein; and
(c) preparing a vaccine formulation using the cells of (b).

In another aspect, the present disclosure provides, in at least one embodiment, a method of preparing a vaccine against a pathogenic bacterial infection comprising:
(a) providing a pathogenic bacterial strain comprising a nucleic acid sequence encoding a SLAM polypeptide;
(b) impairing SLAM production in the pathogenic strain to obtain a SLAM impaired pathogenic bacterial strain; and
(c) using the SLAM impaired pathogenic strain to formulate a vaccine.

In another aspect, the present disclosure provides, in at least one embodiment, a vaccine preparation made according to any of the methods of the present disclosure.

In another aspect, the present disclosure provides, in at least one embodiment, a use of a vaccine preparation made according to any of the methods of the present disclosure to immunize a host organism.

In some embodiments, the vaccine preparation provides protection against an infectious disease mediated by a bacterial organism.

In another aspect, the present disclosure provides, in at least one embodiment, a screening method for identifying a candidate compound for use in the treatment of patients infected by a pathogenic bacterial species, the method comprising:
(a) providing a test compound;
(b) comparing in a functional assay the effect of the test compound with a control on the function of a SLAM polypeptide in the pathogenic bacterial species; and
(c) identifying a test compound exhibiting an effect on the native function of a SLAM polypeptide.

In some embodiments, the pathogenic bacterial species belongs to the genus *Neisseria*.

In another aspect, the present disclosure provides, in at least one embodiment, a method for identifying a target protein capable of being transported by a SLAM polypeptide from the cytosol to the extracellular surface of a cell, the method comprising:
(a) providing a genomic nucleotide sequence comprising
  (i) a first nucleotide sequence encoding a SLAM polypeptide; and
  (ii) a second nucleotide sequence sufficiently long to encode a polypeptide and naturally attached to the first nucleotide sequence;
(b) evaluating the second nucleotide sequence to identify a polypeptide encoding sequence within the second nucleotide sequence; and
(c) using the polypeptide encoding sequence to express the polypeptide in a host cell comprising a SLAM polypeptide to determine whether the protein is transported from the cytosol to the extracellular surface of the host cell, to thereby identify whether the protein is a target protein.

In some embodiments, the first nucleotide sequences comprises a sequence selected from any one of the odd-numbered SEQ ID NOs: SEQ ID NO 1 to SEQ ID NO: 695 set forth herein.

Figure 3:
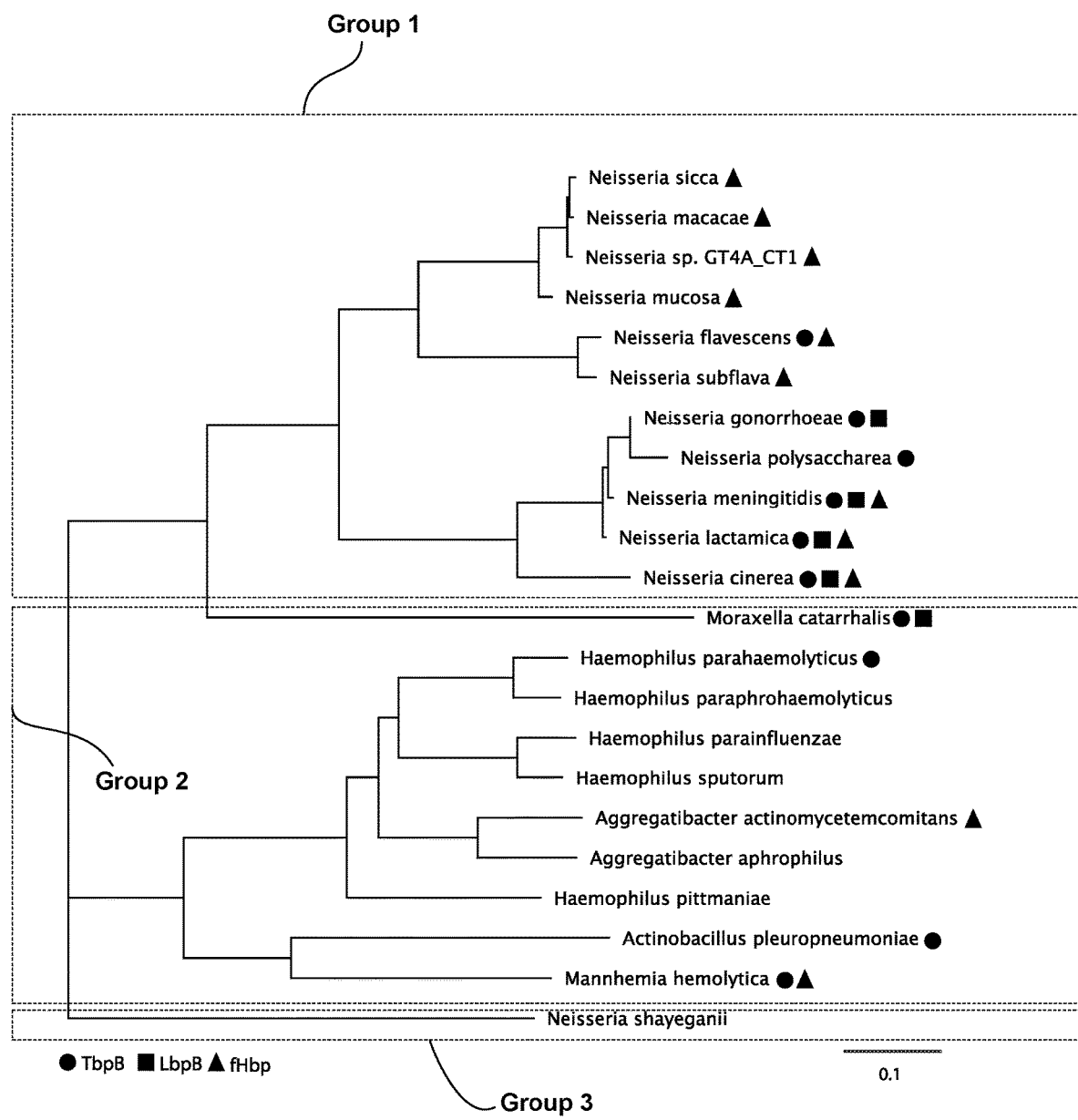

Other features and advantages of the present disclosure will become apparent from the following detailed description. It should be understood, however, that the detailed description, while indicating preferred embodiments of the disclosure, are given by way of illustration only, since various changes and modifications within the spirit and scope of the disclosure will become apparent to those of skill in the art from the detailed description.

BRIEF DESCRIPTION OF THE DRAWINGS

The disclosure is in the hereinafter provided paragraphs described in relation to its Figures. The Figures provided herein are provided for illustration purposes and are not intended to limit the present disclosure.

FIG. 1 shows a diagram outlining a methodology for purification of SLAMs. Step 1: Cells transformed with a plasmid containing 5H3 are grown at 37° C. until the desired optical density is reached. At this point expression is induced with the addition of IPTG. Step 2: After overnight growth, cells are harvested by centrifugation. Cells are then lysed by sonication in the presence of lysozyme and DNAse. Step 3: The membrane fraction of the lysate is isolated through ultracentrifugation. Step 4: The membrane pellet is resuspended and membrane proteins are extracted from the membrane overnight in 50 mM potassium phosphate (pH 7.5, 3% Elugent and PMSF). Step 5: The extraction solution is loaded onto a nickel-NTA column. The column is washed with increasing amounts of imiziadole before 5H3 is eluted from the column with all buffers containing 0.6ˆC8E4. Step 6: Concentrated fractions containing 5H3 are loaded onto a gel filtration column for further purification and detergent exchange. Step 7: Fractions containing 5H3 are pooled and concentrated and the protein is used in subsequent crystal screens.

FIGS. 2A-C shows an overview of the various stages of SLAM1 purification and crystallization. FIG. 2A: Size-exclusion chromatography (SEC) using a S200 column. FIG. 2B The peak containing SLAM1 was analyzed using coomassie stained SDS-PAGE and further concentrated and used for crystallization trials using commercially available screens. FIG. 2C Initial crystal hits are shown for SLAM1.

FIG. 3 shows a phylogenetic tree and the phylogenetic relationships of various SLAM polypeptide homologs in various bacterial species. The SLAM homologs in Group 1 ("Group 1") belong to the *Neisseria* genus and *Moraxella catarrhalis*, while Group 2 ("Group 2") contains different members from the Pasteurellaceae family of Gamma-proteobacteria. Group 3 ("Group 3") contains only *Neisseria shayeganii*.

FIGS. 4A-E shows an overview of the various stages of SLAM2 purification and crystallization. FIG. 4A: Construct used for purification contains a N-terminal pelB sequence (for protein localization) and 6xHis tag (for NiNTA purification). FIG. 4B: The different fractions collected after NiNTA purification shows that eluted fractions contain SLAM2. FIG. 4C: Western blots of fractions confirm the presence of a His tag with an expected mol. weight of SLAM2. Boiled and unboiled fractions were tested. FIG. 4D: Following NINTA purification, samples were further purified using size-exclusion chromatography (SEC) using a S200 column. The figure shows the profile obtained from the SEC run. The peak containing SLAM2 was further concentrated and used for crystallization trials using commercially available screens. FIG. 4E: Initial crystal hits are shown for SLAM2.

FIGS. 5A-C shows N-terminal and C-terminal portions of the SLAM 1 polypeptide (FIG. 5A), and results obtained in the evaluation of translocation of surface lipoproteins using a *Neisseria meningitidis* knock-out strain transformed with SLAM1 and portions thereof and flow cytometry (FIG. 5B) and proteinase K digestion results (FIG. 5C)

FIGS. 6A-C shows results obtained following expression of SLAM 1 in *E. coli* in conjunction with SLPs. Shown are quantitative fluorescence (histograms) and Western blots showing translocation. Shown are results obtained using TbpB (FIG. 6. A), LbpB (FIG. 6B) and fHbp (FIG. 6C). Histograms display the mean fluorescent intensity measured for each sample after incubation with either human transferrin or SLP specific antibody followed by incubation with a secondary fluorescent molecule.

FIGS. 7A-E shows results obtained in the evaluation of SLAM impaired *Neisseria* strains. FIG. 7A shows a solid phase binding assay consisting of *N. meningitidis* cells fixed with paraformaldehyde (PFA) or lysed with SDS, spotted onto nitrocellulose and probed with α-TbpB antibodies. ASLAM/tn5 refers to the original strain of SLAM deficient cells obtained through transposon insertion. ASLAM describes the knockout of SLAM in *N. meningitidis* obtained by replacing the SLAM open reading frame (ORF) with a kanamycin resistance cassette. FIG. 7B shows a Proteinase K digestion assay showing the degradation of TbpB, LbpB and fHbp only when Nm cells are SLAM deficient (ASLAM). *N. meningitidis* cells expressing individual SLPs alone and with SLAM were incubated with proteinase K and Western blots were used to detect levels of all three SLPs levels with and without protease digestion (+/−). Flow cytometry was used to confirm that ΔSLAM cells could not display TbpB (FIG. 7C) or fHbp (FIG. 7D) on the cell surface. Antibodies against TbpB and fHbp were used to bind surface exposed SLPs followed by incubation with a secondary α-Rabbit antibody linked to phycoerythrin to provide fluorescence. The mean fluorescence intensity (MFI) of each sample was measured using the FL2 detector of a BD FACS Calibur. The signal obtained from wildtype cells was set to 100% for comparison with signals from knockout cells. Error bars represent the standard error of the mean (SEM) from three experiments. Shown in FIG. 7E are the results of mice infections with various strains. Mice were infected via intraperitoneal injection with $1×10^6$ CFU of wildtype *N. meningitidis* strain B16B6, B16B6 with a knockout of TbpB (ΔtbpB), or B16B6 with a knockout of nmb0313 Aslam and monitored for survival and disease symptoms every 12 h starting 48 hr pre-infection to 48 h post-infection and additionally monitored at 3 hr post-infection. Statistical differences in survival were assessed by a Mantel-Cox log rank test (GraphPad Prism 5) (*$p<0.05$, n.s. not significant).

FIG. 8 shows a phylogenetic tree comprising exemplary microorganisms which may be used in accordance with the present disclosure. The predicted number of SLAM proteins in the noted bacterial species are shown in parenthesis.

FIGS. 9A-B shows the existence of SLAM family proteins across Gram-negative bacterial species. FIG. 9A shows the domain architecture of *N. meningitidis* SLAM1, possessing two domains: a periplasmic N-terminal domain (Ntd) containing tetratricopeptide repeats and a membrane bound 14-stranded barrel domain referred to as DUF560. FIG. 9B shows the distribution of SLAM proteins in Proteobacteria. A family tree of Proteobacteria was made using 16S-RNA sequences from 55 species representing the major bacterial families within Proteobactria. The families containing at least one species with a SLAM homolog are highlighted by black dots. SLAM homologs were found within all clades of Proteobacteria.

FIGS. 10A-D shows the translocation of SLAM and TbpB pairs from *Moraxella catarrhalis* and *Haemophilus influenzae* in *Escherichia coli*. FIG. 10A shows the SLAM and TbpB gene cluster in *M. catarrhalis* and *H. influenzae*. From the bioinformatics analysis performed, SLAM was found adjacent to known transferrin binding surface lipoprotein TbpB in both human pathogens. FIG. 10B shows the schematic diagram of the *E. coli* translocation assay used in this study. Briefly, SLAM and TbpB genes were expressed in *E. coli* C43 (DE3) cells. The cells were labeled with biotinylated human transferrin and streptavidin linked to the R-phycoerthyrin (PE). Surface display of TbpB was quantified using Flow Cytometry. FIG. 10C shows the Flow Cytometry profiles of *M. catarrhalis* TbpB (McTbpB) and *H. influenzae* TbpB (HiTbpB) obtained with SLAM (shown in black) or without SLAM (shown in gray). A higher signal was observed in the presence of SLAM, indicating the reliance on SLAM for effective surface expression of SLPs. FIG. 10D shows the mean fluorescence blots for TbpB homologs from *M. catarrhalis* and *H. influenzae* using mean flurourescence intensity. Statistical significant was determined using one-way ANOVA where *** represents $p≤0.001$.

FIGS. 11A-D shows the identification of a SLAM-dependent surface lipoprotein in *Pasteurella multocida*. FIG. 11A shows a SLAM gene cluster in *P. multocida* strain Pm70. PM1515 (shown in black) was identified as a SLAM homolog in our bioinformatics search. PM1514 (shown in gray) was annotated as a hypothetical protein. PM1514 contains a signal peptidase II cleavage site ending with a putative lipobox (ITAC) motif. FIG. 11B shows *P. multocida* gene constructs made for a translocation assay to investigate if PM1514 is a SLAM-dependent SLP. Briefly, PM1514 was cloned with a C-terminal Flag-tag (PM1514-Flag), PM1515 was cloned with an N-terminal His-tag and pelB signal sequence, and PM1515-PM1514-Flag was cloned with both PM1515 and PM1514 regions. FIG. 11C shows the Flow Cytometry profiles of *P. multocida* constructs where all three constructs detailed in FIG. 11B were expressed in *E. coli* C43 (DE3) cells and labeled with α-Flag antibody and a mouse secondary antibody linked to R-phycoerthyrin (PE).

Flow Cytometry profiles of PM1514-Flag (light gray), PM1515 and PM1514-Flag (black) and PM1515-PM1514-Flag (dark gray) are shown. FIG. 11D shows the Mean fluorescence intensity blots quantified using mean fluorescence intensity (MFI) of the *P. multocida* constructs. Statistical significance was determined using one-way ANOVA where *** denotes p≤0.001.

FIGS. 12A-E shows the identification of where a translocation motif lies on TbpB. FIG. 12A shows the *N. meningitidis* TbpB and HpuA constructs used in this study, including wildtype TbpB, wildtype HpuA, TbpB N-lobe, TbpB C-lobe, and the TbpB N-lobe fused to HpuA (Nlobe_HpuA). FIG. 12B shows the translocation efficiency of the N- and C-lobe of TbpB as quantified by Flow Cytometry of *E. coli* C43 (DE3) cells expressing full length or individual lobes of *N. meningitidis* TbpB and *N. meningitidis* SLAM1 after labeling with α-TbpB and rabbit-FITC antibodies. FIG. 12C, 12D and FIG. 12E show the translocation efficiency of Nlobe_HpuA with α-TbpB, α-HpuA, and biotinylated human transferrin, respectively. The ability of SLAM1 and SLAM2 to potentiate the translocation of Nlobe-HpuA to the surface of *E. coli* was tested using Flow Cytometry. α-TbpB and biotinylated human transferrin were used to detect the TbpB N-lobe while HpuA was detected using α-HpuA. Mean fluorescence intensity blots are shown and highlight that swapping the TbpB C-lobe with HpuA swaps the specificity of the construct from SLAM1 to SLAM2. Statistical significance was determined using one-way ANOVA where * denotes p≤0.001, ** denotes p≤0.0001 and n.s. denotes non significant.

FIGS. 13A-F shows that two of the C-terminal strands of SLAM-dependent surface lipoproteins are conserved and necessary for surface display. FIG. 13A shows the general structure of the protein domains found on SLAM-dependent SLPs. This family of proteins contains a flexible handle domain and an eight-stranded barrel domain. The barrel domain is conserved amongst all putative SLAM-dependent SLPs. FIG. 13B shows a schematic of the barrel domain from *N. meningitidis* TbpB where the strands are numbered according to the structure of TbpB from *N. meningitidis* strain B16B6 (PDB ID: 4QQ1). The strands mutated by polyalanine mutations are denoted by B22, B23, B30 and B31. FIG. 13C and FIG. 13D show the translocation efficiency of *E. coli* C43 (DE3) cells expressing one of TbpB wildtype alone, SLAM1 and TbpB wildtype, or SLAM1 and TbpB mutants containing polyalanine mutations in four different beta-barrel strands. Cells were labeled with α-TbpB and biotinylated human transferrin and mean fluorescence intensity blots determined that mutations in the last two strands of the TbpB C-lobe barrel prevent surface display of TbpB. Western blot analysis with α-TbpB and α-His were done to confirm expression of TbpB C-lobe mutants and SLAM1, respectively. FIG. 13E shows a multiple sequence alignment of the last two strands of the C-terminal beta-barrel of SLAM-dependent SLPs with conserved residues highlighted in gray. FIG. 13F shows an overlay of conserved residues on the last two beta-barrel strands in the C-lobe structure of TbpB. The two strands are shown facing each other with the residues inside the barrel domain facing each other while residues outside the barrel are away from one another. The conserved residues cluster together at the center of the barrel domain. Statistical significance was determined using a one-way ANOVA where denotes p≤0.001, **** denotes p≤0.0001 and n.s. denotes non significant.

FIGS. 14A-D shows the identification of a SLAM-dependent surface lipoprotein in *Actinobacter baumannii*. FIG. 14A shows a SLAM gene cluster in *A. baumannii* strain LAC4. AbSLAM (shown in gray) was identified as a SLAM homolog in a bioinformatics search. AbSLP (shown in black) was annotated as a hypothetical protein. FIG. 14B shows *A. baumannii* gene constructs made for a translocation assay to investigate if AbSLP is a Slam-dependent SLP. Briefly, AbSLP was cloned with a C-terminal Flag-tag (AbSLP-Flag), AbSLAM was cloned with an N-terminal His-tag and pelB signal sequence. FIG. 14B (right) shows the Flow Cytometry profiles of *A. baumannii* constructs where both constructs detailed were expressed in *E. coli* C43 (DE3) cells and labeled with □-Flag antibody and a mouse secondary antibody linked to R-phycoerthyrin (PE). FIG. 14C shows the AbSLP crystals that were formed (left) and a cartoon diagram of the identified crystal structure of AbSLP. FIG. 14D shows the PK shaving assay in *A. baumannii.*

DETAILED DESCRIPTION OF THE DISCLOSURE

Various compositions and methods will be described below to provide an example of an embodiment of each claimed subject matter. No embodiment described below limits any claimed subject matter and any claimed subject matter may cover methods, processes, compositions or systems that differ from those described below. The claimed subject matter is not limited to compositions or methods having all of the features of any one composition, method, system or process described below or to features common to multiple or all of the compositions, systems or methods described below. It is possible that a composition, system, method or process described below is not an embodiment of any claimed subject matter. Any subject matter disclosed in a composition, system, method or process described below that is not claimed in this document may be the subject matter of another protective instrument, for example, a continuing patent application, and the applicants, inventors or owners do not intend to abandon, disclaim or dedicate to the public any such subject matter by its disclosure in this document. All publications, patents and patent applications are herein incorporated by reference in their entirety to the same extent as if each individual publication.

Terms and Definitions

Unless defined otherwise, all technical and scientific terms used herein shall have the same meaning as commonly understood by one of ordinary skill in the art to which the disclosure pertains. The following terms shall be understood to have the following meanings.

The interchangeably herein used terms "surface lipoprotein assembly modulator", "SLAM", "SLAM protein", and "SLAM polypeptide" refer to any and all SLAM proteins, including those set forth in any one of the even-numbered SEQ ID NOs: SEQ ID NO: 2 to SEQ ID NO: 694 and SEQ ID NO: 1184, and those comprising a sequence of amino acid residues which (i) are substantially identical to the amino acid sequences constituting any SLAM protein set forth herein; (ii) are encoded by a nucleic acid sequence capable of hybridizing under at least moderately stringent conditions to any nucleic acid sequence encoding any SLAM protein set forth herein or capable of hybridizing under at least moderately stringent conditions to any nucleic acid sequence encoding any SLAM protein set forth herein, but for the use of synonymous codons. The terms further include any SLAM precursor polypeptides.

The term "surface lipoprotein", refers to any and all surface lipoproteins, including those set forth in one of the even-numbered SEQ ID NOs: SEQ ID NO: 696 to SEQ ID NO: 1082, SEQ ID NO: 1094, SEQ ID NO: 1100 and even-numbered SEQ ID NOs: 1116 to SEQ ID NO: 1168, and SEQ ID NO; 1178 set forth herein, and those comprising a sequence of amino acid residues which (i) are substantially identical to the amino acid sequences constituting any surface lipoprotein set forth herein; (ii) are encoded by a nucleic acid sequence capable of hybridizing under at least moderately stringent conditions to any nucleic acid sequence encoding any surface lipoprotein set forth herein or capable of hybridizing under at least moderately stringent conditions to any nucleic acid sequence encoding any surface lipoprotein set forth herein, but for the use of synonymous codons. The term surface lipoprotein, further, can refer to polypeptides comprising the surface lipoprotein box sequence motifs set forth in SEQ ID NO: 1170 and SEQ ID NO: 1174 and those comprising a sequence of amino acid residues which (i) are substantially identical to the amino acid sequences constituting any surface lipoprotein box sequence motif set forth herein; or (ii) are encoded by a nucleic acid sequence capable of hybridizing under at least moderately stringent conditions to any nucleic acid sequence encoding any surface lipoprotein box sequence motif set forth herein or capable of hybridizing under at least moderately stringent conditions to any nucleic acid sequence encoding any surface lipoprotein box sequence motif set forth herein, but for the use of synonymous codons.

The interchangeably herein used terms "transferrin binding protein B", "TbpB protein", "TbpB polypeptide" and "TbpB" refer to any and all TbpB proteins, including those set forth in sequences selected from SEQ ID NO: 806, SEQ ID NO: 828, SEQ ID NO: 868, SEQ ID NO: 1094, and one of the even-numbered SEQ ID NOs: SEQ ID NO: 1148 to SEQ ID NO: 1168 set forth herein and those comprising a sequence of amino acid residues which (i) are substantially identical to the amino acid sequences constituting any TbpB protein set forth herein; (ii) are encoded by a nucleic acid sequence capable of hybridizing under at least moderately stringent conditions to any nucleic acid sequence encoding any TbpB protein set forth herein or capable of hybridizing under at least moderately stringent conditions to any nucleic acid sequence encoding any TbpB protein set forth herein, but for the use of synonymous codons.

The interchangeably herein used terms "lactoferrin binding protein", "LbpB protein", "LbpB polypeptide" and "LbpB" refer to any and all LbpB proteins, including those set forth in sequences selected from SEQ ID NO: 870 or one of the even-numbered SEQ ID NOs: SEQ ID NO: 1138 to SEQ ID NO: 1146 set forth herein 6, and those comprising a sequence of amino acid residues which (i) are substantially identical to the amino acid sequences constituting any LbpB protein set forth herein; (ii) are encoded by a nucleic acid sequence capable of hybridizing under at least moderately stringent conditions to any nucleic acid sequence encoding any LbpB protein set forth herein or capable of hybridizing under at least moderately stringent conditions to any nucleic acid sequence encoding any LbpB protein set forth herein, but for the use of synonymous codons.

The interchangeably herein used terms "Factor H binding protein", "fHbp protein", fHbp polypeptide" and "fHbp" refer to any and all fHbp proteins, including those sequences selected from one of the even-numbered SEQ ID NOS: SEQ ID NO: 1116 to SEQ ID NO: 1136 set forth herein, and those comprising a sequence of amino acid residues which (i) are substantially identical to the amino acid sequences constituting any fHbp protein set forth herein; (ii) are encoded by a nucleic acid sequence capable of hybridizing under at least moderately stringent conditions to any nucleic acid sequence encoding any fHbp protein set forth herein or capable of hybridizing under at least moderately stringent conditions to any nucleic acid sequence encoding any fHbp protein set forth herein, but for the use of synonymous codons.

The interchangeably herein used terms "hemoglobin-haptoglobin binding protein A", "HpuA protein", "HpuA polypeptide" and "HpuA" refer to any and all SLAM proteins, including those set forth in SEQ ID NO: 850, SEQ ID NO: 924, SEQ ID NO: 932, or SEQ ID NO: 1110 and those comprising a sequence of amino acid residues which (i) are substantially identical to the amino acid sequences constituting any HpuA protein set forth herein; (ii) are encoded by a nucleic acid sequence capable of hybridizing under at least moderately stringent conditions to any nucleic acid sequence encoding any HpuA protein set forth herein or capable of hybridizing under at least moderately stringent conditions to any nucleic acid sequence encoding any HpuA protein set forth herein, but for the use of synonymous codons.

The herein interchangeably used terms "polynucleotide encoding a surface lipoprotein assembly modulator"; "polynucleotide encoding a SLAM polypeptide"; and polynucleotide encoding a SLAM protein refer to any and all polynucleotides encoding a SLAM polypeptide, including any SLAM polypeptide and any nucleic acid sequences that encode SLAM precursors, including the polynucleotides set forth in SEQ ID NO: 1 and SEQ ID NO: 3. As used herein "SLAM precursor" refers to a SLAM molecule additionally comprising an N-terminal signal sequence which facilitates export of the polypeptide chain across the cytoplasmic membrane of *E. coli* and other Gram-negative bacterial species. Polynucleotides encoding a SLAM polypeptide further include any and all polynucleotides which (i) encode polypeptides that are substantially identical to the SLAM polypeptide sequences set forth herein; or (ii) hybridize to any SLAM polynucleotides set forth herein under at least moderately stringent hybridization conditions or which would hybridize thereto under at least moderately stringent conditions but for the use of synonymous codons.

The term "polynucleotide encoding a surface lipoprotein" refers to any and all polynucleotides encoding a surface lipoprotein, including any surface lipoprotein, including the polynucleotide set forth in odd-numbered SEQ ID NOs including SEQ ID NO: 695 to SEQ ID NO: 1081, and SEQ ID NO: 1177 set forth herein. Polynucleotides encoding a surface lipoprotein further include any and all polynucleotides which (i) encode proteins that are substantially identical to the surface lipoprotein sequences set forth herein; or (ii) hybridize to any surface lipoprotein polynucleotides set forth herein under at least moderately stringent hybridization conditions or which would hybridize thereto under at least moderately stringent conditions but for the use of synonymous codons.

The terms "polynucleotide encoding TbpB", "a polynucleotide encoding a TbpB protein" and "polynucleotide encoding a TbpB polypeptide", as may be used interchangeably herein, refer to any and all polynucleotides encoding a TbpB protein, including any TbpB protein, including the polynucleotide set forth in SEQ ID NO: 1147. Polynucleotides encoding a surface lipoprotein further include any and all polynucleotides which (i) encode proteins that are substantially identical to the surface lipoprotein sequences set forth herein; or (ii) hybridize to any surface lipoprotein polynucleotides set forth herein under at least moderately stringent hybridization conditions or which would hybridize thereto under at least moderately stringent conditions but for the use of synonymous codons.

The terms "polynucleotide encoding LbpB", "a polynucleotide encoding a LbpB protein" and "polynucleotide encoding a LbpB polypeptide", as may be used interchangeably herein, refer to any and all polynucleotides encoding a LbpB protein, including any LbpB protein, including the polynucleotide set forth in SEQ ID NO: 869. Polynucleotides encoding a surface lipoprotein further include any and all polynucleotides which (i) encode proteins that are substantially identical to the surface lipoprotein sequences set forth herein; or (ii) hybridize to any surface lipoprotein polynucleotides set forth herein under at least moderately stringent hybridization conditions or which would hybridize thereto under at least moderately stringent conditions but for the use of synonymous codons.

The terms "polynucleotide encoding fHbp", "a polynucleotide encoding a fHbp protein" and "polynucleotide encoding a fHbp polypeptide", as may be used interchangeably herein, refer to any and all polynucleotides encoding a fHbp protein, including any fHbp protein, including the polynucleotide set forth in SEQ ID NO: 1115. Polynucleotides encoding a surface lipoprotein further include any and all polynucleotides which (i) encode proteins that are substantially identical to the surface lipoprotein sequences set forth herein; or (ii) hybridize to any surface lipoprotein polynucleotides set forth herein under at least moderately stringent hybridization conditions or which would hybridize thereto under at least moderately stringent conditions but for the use of synonymous codons.

The terms "polynucleotide encoding HpuA", "a polynucleotide encoding a HpuA protein" and "polynucleotide encoding a HpuA polypeptide", as may be used interchangeably herein, refer to any and all polynucleotides encoding a HpuA protein, including any HpuA protein, including the polynucleotide set forth in SEQ ID NO: 931. Polynucleotides encoding a surface lipoprotein further include any and all polynucleotides which (i) encode proteins that are substantially identical to the surface lipoprotein sequences set forth herein; or (ii) hybridize to any surface lipoprotein polynucleotides set forth herein under at least moderately stringent hybridization conditions or which would hybridize thereto under at least moderately stringent conditions but for the use of synonymous codons.

By the term "substantially identical" it is meant that two polypeptide sequences preferably are at least 50% identical, and more preferably are at least 85% identical and most preferably at least 95% identical, for example 96%, 97%, 98% or 99% identical. In order to determine the percentage of identity between two polypeptide sequences the amino acid sequences of such two sequences are aligned, using for example the alignment method of Needleman and Wunsch (Needleman S B, Wunsch C D. 1970. A general method applicable to the search for similarities in the amino acid sequence of two proteins. Journal of molecular biology 48:443-453), as revised by Smith and Waterman (Smith TFaMSW. 1981. Comparison of Biosequences. Advances in Applied Mathematics 2:482-489) so that the highest order match is obtained between the two sequences and the number of identical amino acids is determined between the two sequences. A preferred, broadly applicable, method for accurately aligning two polypeptides involves the Clustal W algorithm (Thompson J D, Higgins D G, Gibson T J. 1994. CLUSTAL W: improving the sensitivity of progressive multiple sequence alignment through sequence weighting, position-specific gap penalties and weight matrix choice. Nucleic acids research 22:4673-4680.), employed with the BLOSUM 62 scoring matrix (Henikoff S, Henikoff J G. 1992. Amino acid substitution matrices from protein blocks. Proc Natl Acad Sci USA 89:10915-10919) using a gap opening penalty of 10 and a gap extension penalty of 0.1. This enables identification of high scoring alignments between two sequences, wherein at least 50% of the total length of one of the two sequences is involved in the alignment. Methods to calculate the percentage identity between two aligned amino acid sequences are generally art recognized and include, for example, those described by Carillo and Lipton (Carrillo H, and D. Lipman. 1989. The Multiple Sequence Alignment Problem in Biology. SIAM Journal on Applied Mathematics 48:1073-1082), and those described in Computational Molecular Biology, Lesk, e.d. Oxford University Press, New York, 1988, Biocomputing: Informatics and Genomics Projects. Generally, computer programs will be employed for such calculations. Computer programs that may be used in this regard include, but are not limited to, GCG (Devereux J, Haeberli P, Smithies O. 1984. A comprehensive set of sequence analysis programs for the VAX. Nucleic acids research 12:387-395), BLASTP, BLASTN and FASTA (Altschul S F, Gish W, Miller W, Myers E W, Lipman D J. 1990. Basic local alignment search tool. Journal of Molecular Biology 215:403-410).

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C. .−16.6 (Log10 [Na+])+0.41(% (G+C)−600/1), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm (based on the above equation)−5° C., followed by a wash of 0.2×SSC/0.1% SDS at 60° C. Moderately stringent hybridization conditions include a washing step in 3×SSC at 42° C. It is understood however that equivalent stringencies may be achieved using alternative buffers, salts and temperatures. Additional guidance regarding hybridization conditions may be found in: Green and Sambrook, Molecular Cloning, a Laboratory Manual, Cold Spring Harbor Laboratory Press, 2012 (32).

The term "chimeric" as used herein in the context of polynucleotides refers to at least two linked polynucleotides which are not naturally linked. Chimeric nucleic polynucleotides include linked polynucleotides of different natural origins. For example, a polynucleotide constituting an *E. coli* bacterial promoter linked to a polynucleotide encoding a *Neisseria* SLAM polypeptide is considered chimeric. In addition chimeric polynucleotides may have the same natural origin but are not naturally linked. Furthermore, non-naturally occurring polynucleotide vectors are chimeric. For example, a polynucleotide constituting a promoter obtained from a particular cell-type may be linked to a polynucleotide encoding a polypeptide obtained from that same cell-type, but not normally linked to the polynucleotide constituting the promoter. Chimeric polynucleotides also include polynucleotides comprising any naturally occurring polynucleotide linked to any non-naturally occurring polynucleotide.

The term "cytosol", as used herein, refers to the internal, generally aqueous portion of a cell, e.g. a bacterial cell, and includes all cellular components that may be present within the cytosol, but specifically excludes the extracellular surface of the cell.

The term "extracellular surface", as used herein, is intended to refer to a cellular surface structure of a cell separating the cytosolic portion of the cell from its exogenous environment. The cellular surface structure can include one or more phospholipid membranes with proteins and/or lipopolysaccharides embedded therein.

The term "host organism", as used herein, refers to human and non-human vertebrate animals, including, without limitation, bovine, porcine, equine, murine, canine, feline, piscine, ovine, hircine, simian and avian animals.

The terms "immunogen" and "immunogenic composition", as interchangeably used herein, are used in their broadest sense to refer to a molecule which contains one or more epitopes that will stimulate the immune response in a host organism to generate a cellular immunogen-specific immune response, or a humoral antibody response. Immunogens include proteins, polypeptides, peptides and immunogenic protein fragments.

The terms "vaccine" and "vaccine composition", as interchangeably used herein, refer to any pharmaceutical composition containing an immunogen, which composition can be used to prevent or treat a disease or condition in a host organism. The terms thus encompass subunit vaccines, i.e., vaccine compositions containing immunogens which are separate and discrete from a whole organism with which the immunogen is associated in nature, and further includes live vaccines.

It should be noted that terms of degree such as "substantially", "essentially" "about" and "approximately" as used herein mean a reasonable amount of deviation of the modified term such that the end result is not significantly changed. These terms of degree should be construed as including a deviation of the modified term if this deviation would not negate the meaning of the term it modifies.

As used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

As used in this specification and the appended claims, the singular forms "a", "an", and "the" include plural referents unless the content clearly dictates otherwise. Thus, for example, reference to "an immunogen" includes a mixture of two or more such agents, reference to "a polypeptide" includes reference to mixtures of two or more polypeptides, reference to "a cell" includes two or more such cells, and the like.

General Implementation

As hereinbefore mentioned, the present disclosure relates to polypeptides and polynucleotides obtainable or obtained from Gram-negative bacterial species, notably polypeptides belonging to a class of proteins known as surface lipoprotein assembly modulators or SLAM proteins.

The polynucleotides encoding SLAM proteins of the present disclosure can be used for expression and production of SLAM proteins in host cells. Such expression of SLAM proteins in host cells, surprisingly, can result in the translocation of another protein, referred herein as the target protein, which is present in the host cell from the cytosolic portion of the host cell to the extracellular surface of the host cell.

Furthermore, the polynucleotides encoding SLAM proteins can be used to prepare vaccine formulations useful for the prevention of infections by pathogenic bacterial species, for example, bacterial species belonging to the genus *Neisseria*.

Furthermore, the polynucleotides encoding SLAM proteins and SLAM proteins can be used in assays to identify chemical compounds useful in the treatment of patients infected by pathogenic bacterial species.

Accordingly, in one aspect, the present disclosure provides, in at least one embodiment, a method of effecting transport of a target protein from the cytosol to the extracellular surface of a host cell comprising the target protein, the method comprising:
  (a) providing a chimeric polynucleotide comprising as operably linked components:
    (i) a polynucleotide capable of controlling expression in the host cell; and
    (ii) a polynucleotide encoding a SLAM polypeptide; and
  (b) introducing the chimeric nucleic acid sequence in the host cell and growing the host cell to produce the SLAM polypeptide, thereby effecting transport of the target protein from the cytosol to the extracellular surface of the host cell.

The polynucleotides encoding SLAM polypeptides in accordance herewith can be obtained from any bacterial species or strain comprising polynucleotides encoding SLAM proteins, including, in particular, any Gram negative bacterial species, including any bacterial species belonging to the phylum of proteobacteria, and further including any bacterial species belonging to the class of alpha-proteobacteria, beta-proteobacteria, gamma-proteobacteria and delta-proteobacteria.

In some embodiments, the polynucleotides encoding SLAM polypeptides can be obtained from bacterial species belonging to a family within the alpha-proteobacteria, for example the families of Sphingomonadaceae, Rhizobiales and Rhodobacteraceae. Exemplary bacterial genera and species within each of these families are all of the species provided in FIG. 8 and FIG. 9.

In some embodiments, the polynucleotides encoding SLAM polypeptides can be obtained from bacterial species belonging to a family within the beta-proteobacteria, for example the families of Neisseriaceae, Burholderiales and Rhodocyclaceae. Exemplary bacterial genera and species within each of these families are all of the species provided in FIG. 8 and FIG. 9.

In some embodiments, the polynucleotides encoding SLAM polypeptides can be obtained from bacterial species belonging to a family within the gamma-proteobacteria, for example the families of Pasteurellaceae, Pseudomonodales, Enterobacteriaceae, Vibrionaceae, Xanthomonadaceae, Cardiobacteriaceae and methylophaga. Exemplary bacterial genera and species within each of these families are all of the species provided in FIG. 8 and FIG. 9.

In some embodiments, the polynucleotides encoding SLAM polypeptides can be obtained from bacterial species belonging to a family within the delta-proteobacteria, for example the family of Desulfovibrionaceae. An exemplary bacterial genus and species within this family is provided in FIG. 8 and FIG. 9.

In some embodiments, the polynucleotides encoding SLAM polypeptides can be obtained from a bacterial species belonging to the species *Neisseria meningitidis, Neisseria gonorrhoeae, Neisseria lactamica, Neisseria cincera, Klebsiella denitrificans, Moraxella catarrhalis, Mannheimia haemolytica, Actinobacillus pleuropneomoniae, Haemophilus somni, Haemophilus influenzae, Pasteurella multocida, Acinetobacter baumannii* or *Vibrio cholerae*.

In some embodiments, the polynucleotides encoding SLAM polypeptides are the polynucleotides comprising or consisting of any one of the odd-numbered SEQ ID NOs set forth herein starting from SEQ ID NO: 1 and ending at and including SEQ ID NO: 693.

In some embodiments, the SLAM polypeptides are polypeptides comprising or consisting of any of the even-numbered SEQ ID NOs starting from SEQ ID NO: 2 and ending at and including SEQ ID NO: 694

In accordance with some aspects of the present disclosure, the polynucleotide encoding the SLAM polypeptide is linked to a polynucleotide capable of controlling expression of the SLAM polypeptide in a host cell. The host cell can be any cell, including any eukaryotic cell, including an animal cell or plant cell, or microbial cell, such as a fungal cell or a bacterial cell.

In some embodiments, the host cell is a bacterial cell.

In some embodiments, the host cell is a Gram-negative bacterial cell.

In some embodiments, the host cell is a cell selected from bacterial cells belonging to the genus *Neisseria, Klebsiella, Moraxella, Mannheimia, Actinobacillus, Haemophilus, Pasteurella, Acinetobacter, Escherichia* or *Vibrio*.

In some embodiments, the host cell is selected from bacterial cells belonging to the species, *Neisseria meningitidis, Neisseria gonorrhoeae, Neisseria lactamica, Neisseria cincera, Klebsiella denitrificans, Moraxella catarrhalis, Mannheimia haemolytica, Actinobacillus pleuropneomoniae, Haemophilus somni, Haemophilus influenzae, Pasteurella multocida, Acinetobacter baumannii* or *Vibrio cholerae*.

In preferred embodiments, the host cell is selected from bacterial cells belonging to the genus *Neisseria*, including *Neisseria meningitidis* and *Neisseria gonorrhoeae*, or *Escherichia coli*.

In accordance with one aspect of the present disclosure, a polynucleotide capable of controlling expression in a host cell is linked to a polynucleotide encoding a SLAM polypeptide. Thus, in one aspect, the present disclosure further provides, in at least one embodiment, a polynucleotide encoding a SLAM polypeptide linked to a polynucleotide capable of controlling expression in a host cell.

Polynucleotides capable of controlling expression in host cells that can be used herein include any transcriptional promoter capable of controlling expression of polypeptides in host cells. Generally, promoters obtained from microbial cells are used when a microbial host is selected in accordance herewith, while a eukaryotic promoter is selected when a eukaryotic host is selected, and so on. Further polynucleotide components capable of controlling expression in a host cell include transcriptional terminators, enhancers and the like, all of which may be included in the chimeric polynucleotides of the present disclosure.

In accordance with the present disclosure, the chimeric polynucleotides of the present disclosure are preferably included in an expression vector which ensures good expression of the SLAM polypeptide in the host cell. Accordingly, the present disclosure includes, in one embodiment, a recombinant expression vector comprising as operably linked components:

(i) a polynucleotide capable of controlling expression in a host cell; and (ii) a polynucleotide encoding a SLAM polypeptide wherein the expression vector is suitable for expression in a host cell. The term "suitable for expression in a host cell" means that the recombinant expression vector comprises the chimeric nucleic acid sequence of the present disclosure linked to genetic elements required to achieve expression in a host cell. Genetic elements that can be included in the expression vector in this regard include a transcriptional termination region, one or more nucleic acid sequences encoding marker genes, one or more origins of replication, and the like. The genetic elements are operably linked, typically as will be known to those of skill in the art, by linking e.g. a promoter in the 5' to 3' direction of transcription to a coding sequence. In preferred embodiments, the expression vector further comprises genetic elements required for the integration of the vector or a portion thereof in the host cell's genome. Pursuant to the present disclosure the expression vector can further contain a marker gene. Marker genes that can be used in accordance with the present disclosure include all genes that allow the distinction of transformed cells from non-transformed cells, including all selectable and screenable marker genes. A marker gene can be a resistance marker such as an antibiotic resistance marker against, for example, kanamycin or ampicillin. Screenable markers that can be employed to identify transformants through visual inspection include, for example, β-galactosidase, β-glucuronidase (GUS) (U.S. Pat. Nos. 5,268,463 and 5,599,670) and green fluorescent protein (GFP) (Niedz R P, Sussman M R, Satterlee J S. 1995. Green Fluorescent Protein—an in-Vivo Reporter of Plant Gene-Expression. Plant Cell Rep 14:403-406), or other protein tags, for example a poly-histidine tag or a Flag tag, as shown in FIG. 11 and FIG. 13.

In accordance with one aspect of the present disclosure, the naturally occurring polynucleotides encoding SLAM can be modified. Thus the naturally occurring polynucleotides can be modified in order to enhance expression of the SLAM polypeptide in a host cell, for example by codon-optimizing the polynucleotide sequence encoding a SLAM polypeptide. Accordingly, the present disclosure further provides a codon optimized polynucleotide encoding a SLAM polypeptide, including the polynucleotide set forth in SEQ ID NO: 1113. The polynucleotide encoding SLAM can further be modified to include a signal sequence to facilitate expression. An exemplary polynucleotide encoding a signal sequence is set forth in SEQ ID NO: 1179, and the corresponding polypeptide signal sequence is set forth in SEQ ID NO: 1180. Thus the present disclosure further includes a chimeric polynucleotide encoding a microbial signal sequence operably linked to a polynucleotide encoding a SLAM polypeptide, as well as the polypeptides encoded by such polynucleotides, including the polynucleotides and polypeptides set forth in SEQ ID NO: 1181 and SEQ ID NO: 1182

One host cell that particularly conveniently can be used is *Escherichia coli*. The preparation of *E. coli* vectors can be accomplished using commonly known techniques such as restriction digestion, ligation, ligation-independent cloning, gel electrophoresis, DNA sequencing, the Polymerase Chain Reaction (PCR), and other methodologies. A wide variety of cloning vectors are available to perform the necessary steps required to prepare a recombinant expression vector including custom vectors that the inventors have developed. Among the vectors with a replication system functional in *E. coli*, are vectors such as the pUC or pET series of vectors, etc. Typically, these cloning vectors contain a marker allowing selection of transformed cells. Polynucleotides can be introduced in these vectors, using for example restriction and ligation enzymes, and the vectors may be introduced in *E. coli* by preparing competent cells, electroporation or using other well known methodologies to a person of skill in the art. *E. coli* can be grown in an appropriate medium, such as Luria-Broth medium and harvested. Recombinant expression vectors may readily be recovered from cells upon harvesting and lysing of the cells. Further, general guidance with respect to the preparation of recombinant vectors and growth of recombinant organisms can be found in, for example: Sambrook et al., Molecular Cloning, a Laboratory Manual, Cold Spring Harbor Laboratory Press, 2001, Third Ed.

The production of the recombinant SLAM polypeptides can occur throughout the growth of the bacterial strain, or can be achieved by induction of expression, using e.g. an inducible promoter, such as the lacZ promoter, after a period of growth to achieve a significant biomass.

In accordance herewith, in some embodiments, the SLAM polypeptide subsequently is recovered, isolated and separated from other host cell components. Thus the present disclosure, in a further embodiment, provides a method of expressing a SLAM polypeptide in a host cell comprising:

(a) providing a chimeric polynucleotide comprising as operably linked components:
  (i) a polynucleotide capable of controlling expression in the host cell; and
  (ii) a polynucleotide encoding a SLAM polypeptide; and
(b) introducing the chimeric nucleic acid sequence in the host cell and growing the host cell to produce the SLAM polypeptide; and
(c) recovering the SLAM polypeptide from the host cell.

SLAM protein recovery can be effected by a variety of different protein purification techniques including, e.g. metal-chelate chromatography, ion-exchange chromatography, size exclusion chromatography, affinity chromatography, hydrophobic interaction chromatography, reverse phase chromatography, gel filtration, etc. Further general guidance with respect to protein purification may for example be found in: Protein Purification: Principles, High Resolution Methods, and Applications Janson J-C. 2013. Protein Purification: Principles, High Resolution Methods, and Application, vol. 54. Wiley. The term "recovered" as used herein means that the polypeptide is obtained in more or less pure form. By "substantially pure" it is meant that the immunogenic protein is separated from other host cell components. In accordance here with the immunogenic protein is at least 95% pure, and more preferably at least 96%, 97%, 98% or 99% pure.

In another aspect, the present disclosure relates to novel SLAM polypeptides. Accordingly the present disclosure provides, in at least one embodiment, a SLAM polypeptide comprising or consisting of SEQ ID NO: 1184, or a polypeptide substantially identical thereto.

In another aspect, the present disclosure relates to novel polynucleotides encoding SLAM polypeptides. Accordingly, the present disclosure provides, in at least one embodiment, a polynucleotide comprising or consisting of SEQ ID NO: 1183.

With respect to the host cell, the SLAM polypeptide can be a SLAM polypeptide naturally present therein, and thus in some embodiments, production of the SLAM polypeptide in the host cell can result in the modulation of the SLAM polypeptide protein concentration in the cells, for example, the concentration of SLAM polypeptide in the cell may increase as a result of the introduction of the chimeric polypeptide sequence. In other embodiments, the produced SLAM polypeptide is not naturally present in the host cells.

The target protein can be any protein, polypeptide or peptide, which can require transportation from the cytosol to the extracellular surface of a host cell. The term "extracellular surface", as used herein, is intended to refer to a cellular surface structure of a cell, separating the cytosolic portion of the cell from its exogenous environment. The cellular surface structure can include one or more phospholipid membranes with proteins and/or lipopolysaccharides embedded therein. In Gram-negative bacteria, the extracellular surface structure comprises an inner phospholipid bilayer membrane and an outer phospholipid bilayer membrane separated from one another by an aqueous periplasmic compartment. Upon transportation from the cytosol to the extracellular surface of the host cell, the target protein coordinates and interacts with the extracellular surface structure of the cell. Such interaction can lead to the exposure of at least a portion of the target protein to the exogenous environment of the cell.

In at least some embodiments, the target protein is an immunogenic protein capable of eliciting an immune response in a host organism.

In at least some embodiments, the target protein is an immunogenic polypeptide, or an immunogenic portion thereof, that is naturally displayed on the exterior surface of a pathogenic microorganism.

In at least some embodiments the immunogenic protein is a surface lipoprotein (SLP) or a portion thereof.

In at least some embodiments, the surface lipoprotein (SLP) comprises or consists of a polypeptide sequence or a portion thereof selected from one of the one of the even-numbered SEQ ID NOs: SEQ ID NO: 696 to SEQ ID NO: 1082, SEQ ID NO: 1094, SEQ ID NO: 1100 and even-numbered SEQ ID NOs: 1116 to SEQ ID NO: 1168, and SEQ ID NO; 1178 set forth herein.

In at least some embodiments, the surface lipoprotein (SLP) comprises or consists of a polypeptide sequence or a portion thereof encoded by a polynucleotide selected from one of the even-numbered SEQ ID NOs starting from SEQ ID NO: 695 and ending at and including SEQ ID NO: 1081 set forth herein.

In at least some embodiments, the target protein is a surface lipoprotein located on a bacterial genome adjacent to a polynucleotide sequence encoding a SLAM polypeptide.

In at least some embodiments, the immunogenic protein is a surface lipoprotein, or an immunogenic portion thereof, selected from the group consisting of a transferrin binding protein B (TbpB), including, in some embodiments, TbpB polypeptides comprising SEQ ID NO: 1148, a hemoglobin-haptoglobin binding protein A (HpuA), including, in some embodiments, HpuA polypeptides comprising SEQ ID NO: 932, a Factor H binding protein (fHbp), including, in some embodiments, fHbp polypeptides comprising SEQ ID NO: 1116 and a lactoferrin binding protein (LbpB), including, in some embodiments, LbpB polypeptides comprising SEQ ID NO: 1138.

In at least some embodiments, the transferrin binding protein B (TbpB) is encoded by a polynucleotide sequence comprising or consisting of SEQ ID NO: 1149.

In at least some embodiments, the lactoferrin binding protein B (LbpB) is encoded by a polynucleotide sequence comprising or consisting of SEQ ID NO: 869

In at least some embodiments, the factor H binding protein (fHbp) is encoded by a polynucleotide sequence comprising or consisting of SEQ ID NO: 1115.

In at least some embodiments, the hemoglobin-haptoglobin binding protein A (HpuA) is encoded by a polynucleotide sequence comprising or consisting of SEQ ID NO: 923.

In at least some embodiments, the target protein is a fusion protein comprising two or more surface lipoproteins or portions thereof. In some embodiments, the target protein is a fusion protein comprising two or polypeptides, or portions thereof, obtained from at least two of the lipoproteins selected from SEQ ID NOs: SEQ ID NO: 696 to SEQ ID NO: 1082, and SEQ ID NO: 1178 set forth herein. In further embodiments, the target protein is fusion polypeptide comprising a portion obtained from at least two of a transferrin binding protein (TbpB), a lactoferrin binding protein (LbpB), a factor H binding protein (fHbp) and hemoglobin-haptoglobin binding protein (HpuA). In some embodiments, the target protein is a fusion polypeptide comprising a first surface lipoprotein fused, at the N-terminal end or at the C-terminal end, to an immunogenic portion a second surface lipoprotein. In a specific embodiment, the target protein is the fusion polypeptide set forth in SEQ ID NO: 1102. The implementation of the use of a fusion polypeptide as a target protein in accordance with the present disclosure is further illustrated in Example 9.

In general, in embodiments hereof where a portion of a TbpB peptide is used, such portion comprises at least (i) a TbpB signal peptide lipo-box, including an anchoring peptide (SEQ ID NO: 1170), and/or (ii) the C-terminal domain of the TbpB polypeptide (SEQ ID NO: 1098).

While a substantial number of target proteins are provided in the present disclosure, new target proteins can be discovered and used in accordance with the present disclosure without departing from the spirit of the present disclosure. Thus the present disclosure is not intended to be limited with respect to the target protein and any target protein can be used in order to carry out the novel methods of the present disclosure. In one embodiment, in order to discover new target proteins, the genomic regions immediately adjacent to a genomic region encoding a SLAM polypeptide can be probed for the presence of polynucleotide sequences encoding polypeptides, and any identified polypeptides can be evaluated as target proteins. Accordingly, in yet another aspect, the present disclosure provides, in at least one embodiment, a method for identifying a target protein capable of being transported by a SLAM polypeptide from the cytosol to the extracellular surface of a cell, the method comprising:
  (a) providing a genomic nucleotide sequence comprising
    (i) a first nucleotide sequence encoding a SLAM polypeptide; and
    (ii) a second nucleotide sequence sufficiently long to encode a polypeptide and naturally attached to the first nucleotide sequence;
  (b) evaluating the second nucleotide sequence to identify a polypeptide encoding sequence within the second nucleotide sequence; and
  (c) using the polypeptide encoding sequence to express the polypeptide in a host cell comprising a SLAM polypeptide to determine whether the protein is transported from the cytosol to the extracellular surface of the host cell, to thereby identify whether the protein is a target protein.

In accordance with the foregoing any genomic nucleotide sequence encoding a SLAM polypeptide can be provided.

In some embodiments a genomic nucleotide sequence from any microbial genome, including, for example, the genomes of a bacterial species belonging to the genus *Neisseria, Klebsiella, Moraxella, Mannheimia, Actinobacillus, Haemophilus, Pasteurella, Acinetobacter, Escherichia* and *Vibrio* is provided. The genomic nucleotide sequence can vary in length and can represent an entire genome or portion or fragment thereof, provided however that the first and second nucleotide sequence are naturally attached, and provided further that the second nucleotide sequence is sufficiently long to comprise a nucleotide sequence encoding a polypeptide.

In some embodiments, the first nucleotide sequences comprises a sequence selected from any one of the odd-numbered SEQ ID NOs: SEQ ID NO 1 to SEQ ID NO: 695.

In general, the second nucleotide sequence, which can be attached on either side or both sides to first nucleotide sequence (i.e. 5' or 3' relative to the SLAM encoding sequence), extends at least 100 nucleotides from the first nucleotide sequence. The second nucleotide sequence can also be longer, for example, it can be at least 250 nucleotides, at least 500 nucleotides, at least 1,000 nucleotides, at least 2,000 nucleotides or at least 5,000 nucleotides in length. In some embodiments, the genomic nucleotide sequence is a visual representation of a nucleotide sequence present on a medium capable of visually displaying nucleotide sequence information, such as a computer screen, screen of a tablet or handheld device, or a print-out of the nucleotide sequence on paper. In order to obtain a genomic nucleotide sequence a polynucleotide can be provided upon isolation thereof from a microbial organism, and the sequence of the polynucleotide can be determined using techniques for nucleotide sequencing well known to the art, and the obtained nucleotide sequence can then be visually represented for evaluation. The nucleotide sequence can be evaluated and analyzed for the presence of open reading frames and coding regions polypeptide encoding sequences using techniques and methods well known to the art, including for example computer software capable of nucleic acid sequence translation such as ExPASy (Gasteiger, E.; Gattiker, A; Hoogland, C; Ivanyi, I; Appel, RD; Bairoch, A (2003). "ExPASy: The proteomics server for in-depth protein knowledge and analysis". Nucleic Acids Research. 31 (13): 3784-8). Upon the identification of a polypeptide encoding sequence within the second nucleic acid, genetic constructs including the polypeptide encoding sequence can be prepared and used for expression in a host cell to determine whether the polypeptide is transported from the cytosol to the extracellular surface of the host cell. Genetic constructs can be prepared by isolating the polypeptide encoding nucleotide sequence from its natural source microbial organism, and introducing it in an expression vector suitable for expression in a host cell. In some embodiments, the polypeptide encoding nucleotide sequence comprises or consists of the genomic nucleotide sequence. The expression vector, in turn, can be introduced into a host cell. The host cell is a cell comprising a SLAM polypeptide which can, in some embodiments, be naturally present therein or, in other embodiments, can be recombinantly expressed in the host cell. In embodiments wherein the polypeptide encoding nucleotide sequence comprises or consists of the genomic sequence, the polypeptide encoding nucleotide sequence and the nucleotide sequence encoding the SLAM polypeptide can be simultaneously introduced into the host cell. In some embodiments, the host cell is an *Escherichia coli* cell. In the event the polypeptide, upon growth of the host cell, and expression of the target protein in the host cell, is transported to the extracellular surface of the host cell to associate with the extracellular surface, the polypeptide is a target protein. The foregoing embodiment of the present disclosure is further illustrated in Example 8 and 10 below.

In at least some embodiments, the target protein is naturally present in the host cell. Accordingly, the present disclosure further comprises a method of effecting transport of a target protein naturally present in the host cell from the cytosol to the extracellular surface of a host cell comprising:
  (a) selecting a host cell comprising a target protein naturally present in the cell;
  (b) providing a chimeric polynucleotide comprising as operably linked components:
    (i) a polynucleotide capable of controlling expression in the host cell; and
    (ii) a polynucleotide encoding a SLAM polypeptide; and
  (c) introducing the chimeric nucleic acid sequence in the host cell and growing the host cell to produce the SLAM polypeptide and effect transport of the target protein from the cytosol to the extracellular surface.

In at least at least some embodiments, the target protein is naturally present in a cell of a pathogenic bacterial species selected from the group of bacteria consisting of *Neisseria meningitidis, Neisseria gonorrhoeae, Neisseria lactamica, Neisseria cincera, Klebsiella denitrificans, Moraxella catarrhalis, Mannheimia haemolytica, Actinobacillus pleuropneomoniae, Haemophilus somni, Haemophilus influenzae, Pasteurella multocida, Acinetobacter baumannii* or *Vibrio cholerae.*

In at least some embodiments, the target protein interacts and coordinates with the SLAM polypeptide in a non-covalent manner. The non-covalent interaction between the SLAM polypeptide and the target protein can lead to the formation of a heterodimeric protein complex comprising the SLAM polypeptide and the target protein. The interaction can be a temporary interaction, e.g. for a period of time sufficiently long to permit transport the target polypeptide from the cytosol from the cytosol to the extracellular surface, or a more prolonged interaction wherein the non-covalent interaction between the SLAM polypeptide and the target protein remains upon transport of the target polypeptide to the extracellular membrane of the cell.

In at least some embodiments the target protein is not naturally present in the host cell. Accordingly, the present disclosure further provides, in at least one embodiment, a method of effecting transport of a target protein from the cytosol to the extracellular surface of a host cell comprising:
  (a) providing a first chimeric polynucleotide comprising as operably linked components:
    (i) a polynucleotide capable of controlling expression in the host cell; and
    (ii) a polynucleotide encoding a SLAM polypeptide; and
  (b) providing a second chimeric polynucleotide comprising as operably linked components:
    (i) a polynucleotide capable of controlling expression in the host cell; and
    (ii) a polynucleotide encoding a target protein; and
  (b) introducing the first and second chimeric polynucleotide in the host cell and growing the host cell to produce the SLAM polypeptide and the target protein.

In at least some embodiments, the target protein is covalently linked to the SLAM polypeptide. Accordingly, the present disclosure provides, in at least one embodiment, a method of effecting transport of a target protein from the cytosol to the extracellular surface of a host cell comprising:
  (a) providing a chimeric polynucleotide comprising as operably linked components:
    (i) a polynucleotide capable of controlling expression in the host cell
    (ii) a polynucleotide encoding a SLAM polypeptide; and
    (iii) a polynucleotide encoding a target protein; and
  (b) introducing the chimeric nucleic acid sequence in the host cell and growing the host cell to produce the SLAM polypeptide and effect transport of the target protein from the cytosol to the extracellular surface.

In at least some embodiments, the chimeric polynucleotide is constructed in a manner that results in covalent linking, preferably through a peptide bond, of the N-terminal end of a target protein to the C-terminal end of the SLAM polypeptide.

In at least some embodiments, the chimeric polynucleotide is constructed in a manner that results in the covalent linking, preferably through a peptide bond, of the N-terminal end of the SLAM polypeptide to the C-terminal end of the target protein.

In at least some embodiments the chimeric polynucleotide is constructed in a manner that results in the removal of a portion of the SLAM polypeptide and replacement thereof with the target polypeptide. In some embodiments, the chimeric polynucleotide is constructed in a manner that results removal of at least 1, 2, 3, 4, 5, 6, 7, 8, 9, or 10 amino acid residues of the N-terminal end of the SLAM polypeptide and replacement of such residue(s) with the target protein. In some embodiments, the chimeric polynucleotide is constructed in a manner that results in the removal of at least 1, 2, 3, 4, 5, 6, 7, 8, 9, or 10 amino acid residues of the C-terminal end of the SLAM polypeptide and replacement of the residue(s) with the target protein. In some embodiments, the chimeric polynucleotide is constructed in a manner that results in the insertion of the target protein within the polypeptide sequence of the SLAM polypeptide. In some embodiments, the chimeric polynucleotide is constructed in a manner that results in the insertion of the target protein within the SLAM polypeptide and the replacement of at least 1, 2, 3, 4, 5, 6, 7, 8, 9, or 10 amino acid residue(s) of the SLAM polypeptide by the target protein.

In at least some embodiments, the polynucleotide encoding the SLAM polypeptide can be substantially truncated. Notably the N-terminal portion of the SLAM polypeptide can be removed to obtain a truncated SLAM polypeptide consisting of only the C-terminal domain ß-barrel domain, consisting of 12-14 outer membrane spanning strands. An example of a truncated SLAM polypeptide that may be used in accordance herewith to effect transport of a target protein is set forth in SEQ ID. NO: 1111 and SEQ ID NO: 1112.

In accordance with another aspect hereof, the present disclosure provides, in certain embodiments, methods or preparing vaccines. Accordingly, the present disclosure further provides, in at least one embodiment, a method of preparing a vaccine comprising:

(a) selecting a host cell capable of producing an immunogen
(b) providing a chimeric polynucleotide comprising as operably linked components:
   (i) a polynucleotide capable of controlling expression in the host cell; and
   (ii) a polynucleotide encoding a SLAM polypeptide; and
(c) introducing the chimeric nucleic acid sequence in the host cell and growing the host cell to produce the SLAM polypeptide and the immunogen; and
(d) attenuating the host cell to prepare an attenuated host cell; and
(e) preparing a vaccine formulation comprising the attenuated host cell.

In some embodiments, the host cell is a microbial cell.

In some embodiments, the host cell is a pathogenic microbial cell.

In some embodiments, the host cell is a pathogenic microbial cell mediating an infectious disease.

In at least one embodiment, the host cell is a cell selected from the group of cells consisting of *Neisseria meningitidis, Neisseria gonorrhoeae, Neisseria lactamica, Neisseria cincera, Klebsiella denitrificans, Moraxella catarrhalis, Mannheimia haemolytica, Actinobacillus pleuropneomoniae, Haemophilus somni, Haemophilus influenzae, Pasteurella multocida, Acinetobacter baumannii* and *Vibrio cholerae*. The immunogen may be naturally present in the host cell or it may be recombinantly expressed in the host cell. In order to achieve attenuation, the cells, upon production of the SLAM protein and the immunogen are treated in such a manner that they are no longer capable of infection. Typically this achieved by heat-killing of the bacterial cells or by creating outer membrane vesicles. Attenuation techniques will be generally known to those of skill in the art and can, for example, be found in: Vaccination with attenuated *Neisseria meningitidis* strains protects against challenge with live Meningococci, Li Y, Sun Y H, Ison C, Levine M M, Tang C M. Infect Immun. 2004 January; 72(1):345-51. Li Y, Zhang Q Winterbotham M, Mowe E, Gorringe A, Tang C M. Immunization with live *Neisseria* lactamica protects mice against meningococcal challenge and can elicit serum bactericidal antibodies. Infect Immun. 2006; 74(11):6348-55. Dalseg R, Wedege E, Holst J, Haugen I L, Høiby E A, Haneberg B. Outer membrane vesicles from group B are strongly immunogenic when given intranasally to meningococci mice. Vaccine. 1999; 17:2336-2345.

In at least some embodiments, the present disclosure provide a method of preparing a vaccine comprising:
(a) providing a first chimeric polynucleotide comprising as operably linked components:
   (i) a polynucleotide capable of controlling expression in the host cell;
   (ii) a polynucleotide encoding a SLAM polypeptide; and
(b) providing a second chimeric polynucleotide comprising as operably linked components:
   (i) a polynucleotide capable of controlling expression in the host cell; and
   (ii) a polynucleotide encoding a target protein; and
(c) introducing the first and second chimeric polynucleotide in the host cell and growing the host cell to produce the SLAM polypeptide and the target protein; and
(d) preparing a vaccine formulation comprising the cells of (c).

In at least some embodiments, the present disclosure provides a method of preparing a vaccine comprising:
(a) providing a chimeric polynucleotide comprising as operably linked components:
   (i) a polynucleotide capable of controlling expression in the host cell;
   (ii) a polynucleotide encoding a SLAM polypeptide; and
   (iii) a polynucleotide encoding a target protein; and
(b) introducing the chimeric polynucleotide in the host cell and growing the host cell to produce the SLAM polypeptide and the target protein; and
(c) preparing a vaccine formulation comprising the cells of (b).

In a at least some embodiments, present disclosure further provides a method of preparing a vaccine against a pathogenic bacterial infection comprising:
(a) providing a pathogenic bacterial strain comprising a nucleic acid sequence encoding a SLAM polypeptide;
(b) impairing SLAM production in the pathogenic strain to obtain a SLAM impaired pathogenic bacterial strain; and
(c) using the SLAM impaired pathogenic strain to formulate a vaccine.

In preferred embodiments, the pathogenic bacterial strain is a strain of *Neisseria meningitidis, Neisseria gonorrhoeae, Neisseria lactamica, Neisseria cincera, Klebsiella denitrificans, Moraxella catarrhalis, Mannheimia haemolytica, Actinobacillus pleuropneomoniae, Haemophilus somni, Haemophilus influenza, Pasteurella multocida, Acinetobacter baumannii* or *Vibrio cholera*.

In at least some embodiments the pathogenic bacterial strain is a bacterial strain belonging to the genus *Neisseria*. In accordance with the foregoing, any bacterial *Neisseria* strain can be used. In order to impair the *Neisseria* strain any methodology can be used. Preferably, a method which results in the attenuation or the knock-out of the genomic polynucleotide sequence encoding a SLAM polypeptide is used, for example by transposon mutagenesis. Thus in preferred embodiments a SLAM impaired *Neisseria* strain, is a *Neisseria* strain in which a genomic polynucleotide encoding SLAM polypeptide has been mutated in such a manner that no substantive amounts of SLAM polypeptide are produced, such mutation can include the removal of the a polynucleotide encoding a SLAM polypeptide.

In another aspect, the present disclosure provides, in at least one embodiment, a pathogenic bacterial strain comprising an impaired genomic SLAM polynucleotide sequence. With the term "strains comprising impaired genomic SLAM polynucleotide sequence", it is meant that a bacterial strain is not capable of producing substantive amounts of SLAM polypeptide. In some embodiments, the pathogenic bacterial strain is a *Neisseria* strain. This includes strains comprising polynucleotides in which the open reading frame has been interrupted, and strains regulating expression of SLAM proteins are not functional, and the term is further intended to include strains from which a genomic SLAM encoding polynucleotide sequence has been removed. Thus the disclosure further includes a mutant pathogenic bacterial strain lacking a genomic polynucleotide sequence encoding a SLAM polypeptide. In preferred embodiments, the mutated pathogenic bacterial strain is a *Neisseria* strain. In accordance with the foregoing, it is intended that the mutant strain lacks at least one genomic polynucleotide encoding a SLAM polypeptide when compared to the native strain. In preferred embodiments, the mutant *Neisseria* strain is a *Neisseria meningitidis* strain or a *Neisseria gonorrhoeae* strain.

In accordance with certain aspects of the present disclosure, a vaccine preparation is prepared. The vaccine can be used to administer to a host organism, including any human and non-human animal, including without limitation any bovine, porcine, equine, murine, canine, feline, piscine, ovine, hircine, simian and avian animals. Accordingly, in another aspect, the present disclosure provides, in at least one embodiment, a vaccine preparation prepared according to any of the methods of the present disclosure.

In another aspect, the present disclosure provides, in at least one embodiment, a use of a vaccine preparation made according to any of the methods of the present disclosure to immunize a host organism.

In some embodiments, the vaccine preparation can be used to immunize a host organism against an infectious disease mediated by a bacterial organism belonging to the genus, *Neisseria, Klebsiella, Moraxella, Actinobacillus, Haemophilus, Pasteurella, Acinetobacter* or *Vibrio cholerae.*

In some embodiments, the vaccine preparation can be used to immunize a host organism against an infectious disease mediated by a bacterial organism belonging to the species, *Neisseria meningitidis, Neisseria gonorrhoeae, Neisseria lactamica, Neisseria cincera, Klebsiella denitrificans, Moraxella catarrhalis, Mannheiia haemolytica, Actinobacillus pleuropneomoniae, Haemophilus somni, Haemophilus influenzae, Pasteurella multocida, Acinetobacter baumannii* or *Vibrio cholerae.*

In at least some embodiments, of the present disclosure, the vaccines, when administered to a human prevent infection by *Neisseria* bacteria, notably *Neisseria meningitidis* and *Neisseria gonorrhoeae*. In accordance here with vaccine formulations may be prepared using the cells prepared using the methods of the present disclosure. In some embodiments, the vaccine formulations can be prepared using attenuated cells. In other embodiments, the cells may be used as source from which certain fractions, for example a protein fraction or a membrane may be obtained and used to prepare a vaccine. Vaccine preparations of the present disclosure preferably further comprise vehicles, excipients and auxiliary substances, such as wetting or emulsifying agents, pH buffering substances and the like. These vehicles, excipients and auxiliary substances are generally pharmaceutical agents that do not induce an immune response in the recipient subject, and that can be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, phosphates, sulfates, and the like; and the salts of organic acids such as acetates, propionates, benzoates, and the like. It is also preferred, although not required, that the preparation will contain a pharmaceutically acceptable excipient that serves as a stabilizer, particularly in order to stabilize the polypeptides of the present disclosure. Examples of suitable carriers that also act as stabilizers for peptides include, without limitation, pharmaceutical grades of dextrose, sucrose, lactose, sorbitol, inositol, dextran, and the like. Other suitable carriers include, again without limitation, starch, cellulose, sodium or calcium phosphates, citric acid, glycine, polyethylene glycols (PEGs), and combinations thereof. In order to augment an immune response in a subject, the compositions provided herein further preferably include adjuvants, such as pharmacological agents, cytokines, or the like. Suitable adjuvants include any substance that enhances the immune response of the subject to the immunogenic polypeptides of the disclosure. Non-limiting examples of adjuvants include cytokines, e.g., IL-1, IL-2, IL-12, IL-6, and further include inorganic salts, e.g. aluminum hydroxide, aluminum phosphate, and calcium phosphate; oil emulsions, e.g. mineral oil, MF59, QS-21, Montamide ISA51 and ISA-720; Isocoms, e.g. ISCOMATRIX; microbial derivatives, e.g. MPLA, macrophage-activating protein-2, virosomes, LT/CT, CpG; natural polymers, e.g. polysaccharides; and synthetic polymers, e.g. polyanhydrides and polyesters, as reviewed in Wilson-Welder et al. (Wilson-Welder J H, Torres M P, Kipper M J, Mallapragada S K, Wannemuehler M J, Narasimhan B. 2009. Vaccine Adjuvants: Current Challenges and Future Approaches. J Pharm Sci-Us 98:1278-1316). Adjuvants may be administered, for example, as proteins or other macromolecules at the same time, prior to, or subsequent to, administration of the attenuated cells.

The present disclosure still further provides a screening method for identifying a candidate compound for use in the treatment of patients with a infected by a pathogenic bacterial species, the method comprising:

(a) providing a test compound;

(b) comparing in a functional assay the effect of the test compound with a control on the native function of a SLAM polypeptide in the pathogenic bacterial species; and (c) identifying a test compound exhibiting an effect on the native function of a SLAM polypeptide.

In preferred embodiments, the pathogenic bacterial species belongs to the genus *Neisseria.*

In accordance with the foregoing a chemical compound may be evaluated for its utility to treat patients with a *Neisseria* infection. Typically this is achieved by providing one or a more compounds that one wishes to test and the performance of a functional assay. The assay is preferably an in-vitro assay, and can be configured so that multiple compounds can be evaluated simultaneously. The functional assay can be any assay that is capable of detecting an effect on the native function of a SLAM polypeptide. For example, the assay can involve evaluation of the transport of a target protein to the cellular surface in the presence of the chemical compound, notably comparison of transport in the presence of a negative control (e.g. an innocuous compound) or a positive control (i.e. a compound known to having an effect on function of SLAM proteins). Thus for example, TbpB transport can be monitored upon selecting a chemical compound exhibiting an effect on the native function of a SLAM polypeptide, further evaluation of the selected compound may include testing of the compound in in vitro or in vivo tests, including administration of the chemical compound to a human Hereinafter are provided examples of specific embodiments for performing the methods of the present disclosure, as well as embodiments representing the compositions of the present disclosure. The examples are provided for illustrative purposes only, and are not intended to limit the scope of the present disclosure in any way.

EXAMPLES

Example 1—Isolation of a Polynucleotide Encoding a SLAM Polypeptide (SLAM 1)

In vitro transposition of N.men-B16B6 genomic DNA was performed using a EZ::TN<KAN2> Transposon kit (Epicentre). Approximately 400 ng of sonicated DNA (1-6 kb) was mixed with 10 µl of transposase in a 100 µl reaction and incubated at 37° C. for 2 hours. EZTN5-Stop solution was added and incubated at 70° C. for 10 minutes. After concentration by ethanol precipitation, the DNA was repaired with T4 DNA polymerase and T4 ligase (V. pelicic, S. Morelle, D. Lampe, X. Nassif, Journal of Bacteriology, 182: 5391 (Oct. 1, 2000)).

The transposon was introduced to B16B6 by spot transformation (T. H. Dillard et al. Surg. Obes. Rel. Dis. 9: 269 (Jan. 1, 2013)). Briefly, the reaction mix was spotted on a Brain Heart Infusion (BHI) plate where N.men-B16B6 colonies were used to streak the entire plate including the spots. The plate was incubated at 37° C. with 5% $CO_2$ for 8 hours or until colonies appeared. The meningococci grown on the spots were plated on BHI plates containing kanamycin (80 µg/mL) and incubated overnight. Transposon mutants were collected into microtiter plates and grown in liquid BHI for 6 hours before freezing at -80° C. in BHI with 20% glycerol.

Transposon mutants were screened for the presence of surface TbpB by dot blot. Whole cells were fixed with 2% formaldehyde in PBS, spotted on nitrocellulose, blocked with 5% skim milk, and incubated with rabbit anti-TbpB antibodies. Mutants that did not show surface TbpB were sequenced by RATE PCR (T. F. Ducey, Dyer D., Epicentre Forum 9, (2002)) or splinkerette PCR (C. J. Potter, L. Luo, PLOS ONE 5, e10168 (Jan. 1, 2010)). For RATE PCR, genomic DNA was mixed with a single primer (inv1 or inv2) for a three step PCR reaction consisting of stringent annealing temperatures in the first round, low annealing temperatures in the second, and stringent annealing temperatures in the third. The resulting product was sequenced with Kan F or Kan R primers. For splinkerette PCR, genomic DNA is digested by restriction enzymes (BstY1, BglII, or HindIII) separately, producing sticky ends that could be ligated to the splinkerette oligonucleotide. The resulting product is used for two nested PCRs to amplify the genomic sequence between the TN5 insertion and the splinkerette. The product is used for sequencing with another nested primer. Using the foregoing approach the polynucleotide encoding SLAM 1 set for the in SEQ ID NO: 385 was obtained.

Restriction free cloning was employed for the following plasmid construct (F van den Ent, J. Lowe, Journal of Biochemical and Biophysical Methods (Jan. 1, 2006)). Briefly, to replace the NMB0313 ORF with a kanamycin cassette, an ~2500 bp fragment containing NMB0313 and 500 bp upstream and downstream of NMB0313 was cloned into pUC19 using F1 (pUC19OmpU476RF) and R1 (pUC19-OmpURev). KAN2 from the EZ:: TN transposon kit was amplified using primers F2 (F-RF-OmpUdKan) and R2 (R-RF-OmpUdKan) and the resulting megaprimer was used to replace the NMB0313 ORF in a secondary RF reaction. The resulting plasmid was used for spot transformation in WT B16B6. Knockouts were selected on BHI plates containing kanamycin (80 µg/mL) and verified by PCR using primers that flank NMB0313.

Complementation vector pSLAM was constructed by cloning the NMB0313 gene into the PacI/FseI site of pGCC4 (I. J. Mehr, C. D. Long, C. D. Serkin, H. S. Siefert, Genetics, 154, 523 (Feb. 1, 2000)) (Gift from H. Siefert) using primers F3 (F-RF-pGOmpU) and R3 (R-RF-pGOmpU). A HIS tag was inserted after the signal peptide by amplifying the whole vector with phosporylated primers F4 (F-OmpU-HIS phos) and R4 (R-OmpU-HIS phos) that contain the HIS tag, and ligating the products. Knockouts and transposon mutants were complemented with pSLAM by spot transformation and selection on erythromycin (30 µg/mL) plates. Insertion of NMB0313 was verified by PCR. Expression was induced by growing colonies on 1 mM IPTG BHI plates and verified by anti-HIS westerns.

Example 2—Purification of a First SLAM Polypeptide (SLAM 1)

Figure 2:
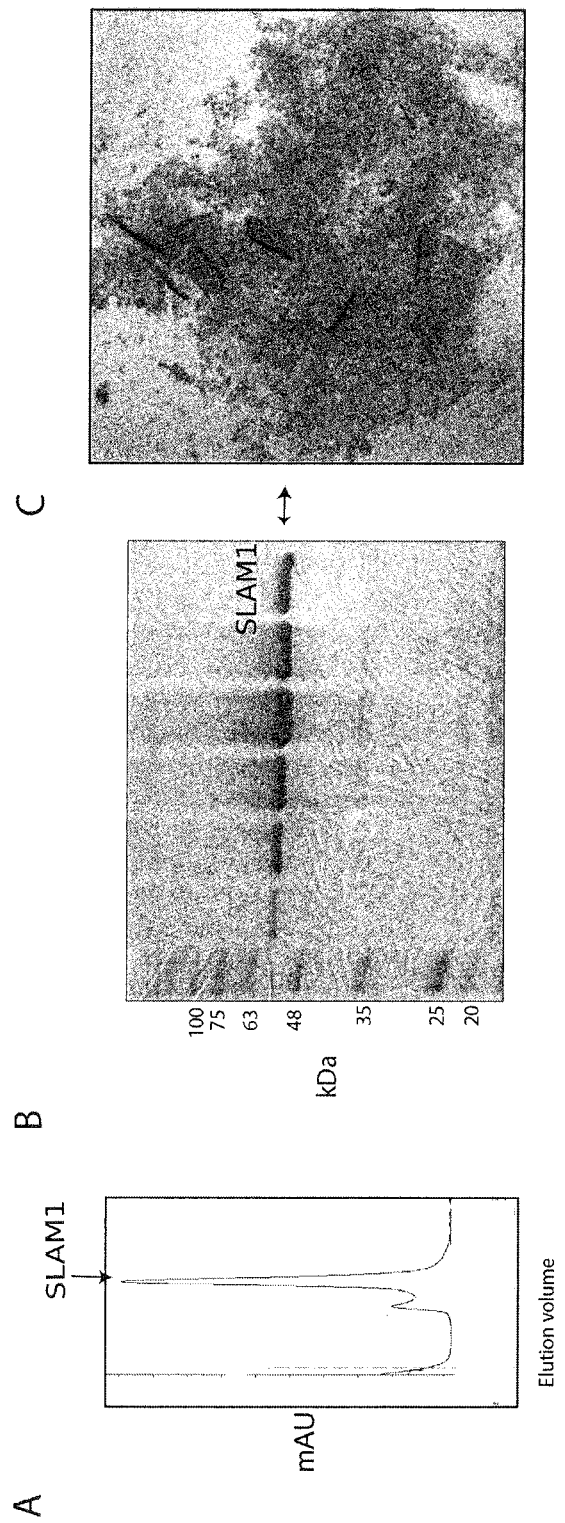

SLAM polypeptides were purified as outlined in FIG. 1. NMB0313 and its homologs were cloned into pET26, and expressed with an N-terminal pelB signal peptide followed by a non-cleavable 7× His tag. The plasmid was transformed into *E. coli* BL21-C43 cells and grown in Luria-Broth (LB) at 37° C. with 50 µg/mL Kanamycin to an OD600 of 0.8, at which point protein expression was induced with the addition of isopropyl β-D-1-thiogalactopyranoside (IPTG) to a final concentration of 1 mM. Cells were grown for an additional 18 hours at 37° C. and were harvested by centrifugation at 4000×g. The cells were washed and resuspended in 100 mL of lysis buffer (50 mM potassium phosphate, pH 7.5 and 0.2 mM PMSF) per 5 g of cells. Cell lysis was carried out by sonication on ice, with four 30 second pulses in the presence of lysozyme and DNase. Unlysed cells were removed by centrifugation at 10,000×g for 20 minutes. The lysate was then centrifuged at 95,834×g for 1 hour to isolate the membrane fraction. The pellet was washed and resuspended in 50 mL of extraction buffer (50 mM potassium phosphate, pH 7.5 and 3% Elugent (Millipore)) per 5 g of cells lysed. The extraction was carried out overnight at 4° C. After a 40 minute centrifugation at 95,834×g, the solubilized protein was passed through a 0.45□m filter and was loaded onto a 1 mL Ni-NTA resin column (GE) equilibrated with Buffer A (50 mM potassium phosphate, 0.6% C8E4 (Affymetrix)). Imidazole gradients were made by mixing buffer A with buffer B (50 mM potassium phosphate, 0.6% C8E4, 400 mM imidazole). The column was washed with 20 mM, 60 mM, and 80 mM imidazole and desired protein was eluted in 260 mM imidazole. Purity was verified by SDS-PAGE and further purification was achieved by size exclusion chromatography with a 24 mL Superdex-200 (GE) equilibrated in 20 mM HEPES, pH 8, 150 mM NaCl, 0.6% C8E4. A single peak containing 5H3 NMB0313 was collected from the Sephadex-200 and was concentrated at 6 mg/mL using a 50 kDa concentrator (Millipore). Results are shown in FIG. 2.

Example 3—Identification of Other Polynucleotides Encoding SLAM Polypeptides, Including SLAM 2

A Blastp search was conducted using the SLAM1 protein sequence (SEQ ID NO: 385) as a template. The results were then filtered to remove SLAM hits from multiple strains of the same organism, and the top hit was kept. The multiple sequence alignments and phylogenetic tree (neighbor-joining) construction was done Geneious using R7 (Biomatters, http://www.geneious.com/). The tree was re-sampled 100 times using the in-built bootstrap module. fHBP, TbpB and LbpB homologs were searched in each of the genomes that contain a SLAM hit, and added to the phylogenetic tree. The phylogenetic tree is shown in FIG. 3. Referring to FIG. 3, SLAM homologs (identified by BLAST searches of bacterial genomes) cluster into three groups. The SLAM homologs in Groups 1 (light gray, top) belong to the *Neisseria* genus and *Moraxella catarrhalis*, while Group 2 (medium gray, middle) contains different members from the Pasteurellaceae family of Gamma-proteobacteria. Group 3 (dark gray, bottom) contains only *Neisseria shayeganii*. The tree has been abbreviated for clarity; multiple hits from a single species were not included, and bootstrap values were removed. Species that possess a TbpB, LbpB, or fHbp homolog in their genome are indicated by circle, square and triangle respectively. The polynucleotide sequence of a second SLAM polypeptide of *Neisseria meningitides*, SLAM 2, is set forth herein as SEQ ID NO: 387.

Example 4—Purification of a Second SLAM Polypeptide (SLAM2)

A second SLAM polypeptide of *Neisseria meningitides* (SLAM 2; SEQ ID NO: 387) was purified using the methodology as further described in Example 2. FIG. 4 shows the results obtained.

Example 5—Surface Lipoprotein Translocation Using an Intact and Truncated SLAM 1 Polypeptide

*Neisseria meningitidis* SLAM knockout strain Δmnb0313 was used to evaluate translocation of: surface lipoproteins (SLPs). Full-length SLAM polypeptides and N-terminal and C-terminal portions of the SLAM polypeptide were used. The N-terminal and C-terminal portions are shown in FIG. 5A. Flow cytometry (FIG. 5B) and proteinase K digestion (FIG. 5C) experiments reveal that the SLP translocation defect observed in the SLAM knockout strain can be rescued with only the C-terminal β-barrel domain (amino acids 204-488). The N-terminal domain (Ntd) (amino acids 32-203) of SLAM does not provide any SLP translocation activity. The mean fluorescent intensity was measured for each sample and the signal obtained from wildtype cells was set to 100% for comparison with signals from knockout and single domain complemented cells. Error bars represent the standard error of the mean (SEM) from three experiments. A * indicates results are significantly different at $p<0.05$.

Example 6—Co-Expression of SLAM and Surface Lipoproteins, TbpB, LbpB and fHbp in *E. coli*

TbpB and NMB0313 genes were amplified from the genome of *Neisseria meningitidis* serotype B strain B16B6. The LbpB gene was amplified from *Neisseria meningitidis* serotype B strain MC58. Full length TbpB was inserted into Multiple Cloning Site 2 of pETDuet using restriction free cloning ((F van den Ent, J. Lowe, Journal of Biochemical and Biophysical Methods (Jan. 1, 2006)).). NMB0313 was inserted into pET26, where the native signal peptide was replaced by that of pelB. Mutations and truncations were performed on these vectors using site directed mutagenesis and restriction free cloning, respectively. Pairs of vectors were transformed into *E. coli* C43 and were grown overnight in LB agar plates supplemented with kanamycin (50 μg/mL) and ampicillin (100 μg/mL).

tbpB genes were amplified from the genomes of *M. catarrhalis* strain O35E and *H. influenzae* strain 86-028NP and cloned into the pET52b plasmid by restriction free cloning as above. The corresponding SLAMs (*M. catarrhalis* SLAM 1, *H. influenzae* SLAM1) were inserted into pET26b also using restriction free cloning. A 6His-tag was inserted between the pelB and the mature SLAM sequences as above. Vectors were transformed into *E. coli* C43 as above.

Cells were harvested by centrifugation at 4000 g and were twice washed with 1 mL PBS to remove any remaining growth media. Cells were then incubated with either 0.05-0.1 mg/mL biotinylated human transferrin (Sigma-aldrich T3915-5MG), α-TbpB (1:200 dilution from rabbit serum for *M. catarrhalis* and *H. influenzae;* 1:10000 dilution from rabbit serum for *N. meningitidis*), or α-LbpB (1:10000 dilution from rabbit serum-obtained a gift from J. Lemieux) or α-fHbp (1:5000 dilution from mouse, a gift from D. Granoff) for 1.5 hours at 4° C., followed by two washes with 1 mL of PBS. The cells were then incubated with R-Phycoerythrin-conjugated Streptavidin (0.5 mg/ml Cedarlane) or R-phycoerythrin conjugated Anti-rabbit IgG (Stock 0.5 mg/ml Rockland) at 25 μg/mL for 1.5 hours at 4° C. The cells were then washed with 1 mL PBS and resuspended in 200 μL fixing solution (PBS+2% formaldehyde) and left for 20 minutes. Finally, cells were washed with 2×1 mL PBS and transferred to 5 mL polystyrene FACS tubes. The PE fluorescence of each sample was measured for PE fluorescence using a Becton Dickinson FACSCalibur. The results were analyzed using FLOWJO software and were presented as mean fluorescence intensity (MFI) for each sample. For *N. meningtidis* experiments, all samples were compared to wildtype strains by normalizing wildtype fluorescent signals to 100%. Errors bars represent the standard error of the mean (SEM) across three experiments. Results were plotted statistically analysed using GraphPad Prism 5 software. The results shown in FIG. 6 for the SLPs, TbpB (FIG. 6A), LbpB. (FIG. 6B) and fHbp (FIG. 6C) demonstrate that SLAM effects translocation of all three SLP polypeptides in *E. coli*. The results shown in FIG. 10 demonstrate that translocation of TbpB from *M. catarrhalis* (FIG. 10C) and in *H. influenzae* (FIG. 10D) in *E. coli* require the co-expression of the required SLAM protein (Slam is an outer membrane protein that is required for the surface display of lipidated virulence factors in *Neisseria*. Hooda Y, Lai C C, Judd A, Buckwalter C M, Shin H E, Gray-Owen S D, Moraes T F. Nat Microbiol. 2016 Feb. 29; 1:16009).

Example 7—Reduction of Virulence of a *Neisseria* Strain Comprising an Impaired SLAM Gene Sepsis modeling was performed as described by Gorringe A. R., Reddin, K. M., Voet P. and Poolman J. T. (Methods Mol. Med. 66, 241 (Jan. 1, 2001)) and Johswich, K. O. et al. (Infect. Immun. 80, 2346 (Jul. 1, 2012)). Groups of 6 eight-week-old C57BL/6 mice (Charles River Laboratories) were inoculated via intraperitoneal injection with *N. meningitidis* strain B16B6, B16B6 Δtbpb, or B16B6 Δnmb0313 (N=2 independent experiments). To prepare inoculums, bacterial strains for infection were grown overnight on GC agar, resuspended and then grown for 4 h in 10 ml of Brain Heart Infusion (BHI) medium at 37° C. with shaking. Cultures were adjusted such that each final 500 μl inoculum contained $1\times10^6$ colony forming units and 10 mg human holo-transferrin. Mice were monitored at least every 12 h starting 48 h before infection to 48 h after infection for changes in weight, clinical symptoms and bacteremia. Mice were scored on a scale of 0-2 based on the severity of the following clinical symptoms: grooming, posture, appearance of eyes and nose, breathing, dehydration, diarrhea, unprovoked behavior, and provoked behavior. Animals reaching endpoint criteria were humanely euthanized. Animal experiments were conducted in accordance with the Animal Ethics Review Committee of the University of Toronto.

FIG. 7 shows the results obtained. FIG. 7A shows a solid phase binding assay consisting of N.men cells fixed with paraformaldehyde (PFA) or lysed with SDS and were spotted onto nitrocellulose and probed with α-TbpB antibodies. ΔSLAM/tn5 refers to the original strain of SLAM deficient cells obtained through transposon insertion. ΔSLAM describes the knockout of SLAM in Neisseria meningitidis obtained by replacing the SLAM ORF with a kanamycin resistance cassette. FIG. 7B shows a Proteinase K digestion assay showing the degradation of TbpB, LbpB and fHbp only when Nm cells are SLAM deficient (ΔSLAM). Nm cells expressing individual SLPs alone and with SLAM were incubated with proteinase K and Western blots were used to detect levels of all three SLPs levels with and without protease digestion (−/+). Flow cytometry was used to confirm that ΔSLAM cells could not display TbpB (FIG. 7C) or fHbp (FIG. 7D) on the cell surface. Antibodies against TbpB and fHbp were used to bind surface exposed SLPs followed by incubation with a α-Rabbit antibody linked to phycoerythrin to provide fluorescence. The mean fluorescent intensity (MFI) of each sample was measured using the FL2 detector of a BD FACS Calibur. The signal obtained from wildtype cells was set to 100% for comparison with signals from knockout cells. Error bars represent the standard error of the mean (SEM) from three experiments. Shown in FIG. 7E are the results of mice infections with various strains. Mice were infected via intraperitoneal injection with $1 \times 10^6$ CFU of wildtype N. meningitidis strain B16B6, B16B6 with a knockout of TbpB (ΔtbpB), or B16B6 with a knockout of nmb0313 Aslam and monitored for survival and disease symptoms every 12 h starting 48 hr pre-infection to 48 h post-infection and additionally monitored at 3 hr post-infection. Statistical differences in survival were assessed by a Mantel-Cox log rank test (GraphPad Prism 5) (*$p<0.05$, n.s. not significant). These results show a marked reduction in post-infection mortality in mice infected with the knockout of nmb0313 Aslam strain.

Example 8: Identification of Novel SLAM-Dependent Surface Lipoproteins in *Pasteurella multocida*

In selecting genomes for a given bacterial species where a SLAM homolog was identified, preference was given to reference genomes that contained fully sequenced genomes. SLAM homologs were identified using iterative Blast searches into closely related species to *Neisseria* to more distantly related species. For each of the SLAM homologs identified in these species, the corresponding genomic record (NCBI genome) was used to identify genes upstream and downstream along with their corresponding functional annotations (NCBI protein database, Ensembl bacteria). In a few cases, no genes were predicted upstream or downstream of the SLAM gene as they were too close to the beginning or end of the contig, respectively, and thus these sequences were ignored.

Neighbouring genes were analyzed for 1) an N-terminal lipobox motif (predicted using LipoP, SignalP), and 2) a solute binding protein, Tbp-like (InterPro signature: IPR or IPR011250), or pagP-beta barrel (InterPro signature: IPR011250) fold. If they contained these elements, we identified the adjacent genes as potential SLAM-dependent surface lipoproteins.

A putative SLAM (PM1515, SEQ ID NO: 1087) was identified in *Pasteurella multocida* using the *Neisseria* SLAM as a search. The putative SLAM (PM1515, SEQ ID NO: 1087) was adjacent to a newly predicted lipoprotein gene with unknown function (PM1514, SEQ ID NO: 1083) (FIG. 11A). The putative SLAM displayed 32% identity to *N. meningitidis* SLAM1 while the SLP showed no sequence similarity to known SLAM-dependent neisserial SLPs.

The putative SLAM (PM1515, SEQ ID NO: 1087) and its adjacent lipoprotein (PM1514, SEQ ID NO: 1083) were cloned into pET26b and pET52b, respectively, as previously described and transformed into *E. coli* C43 and grown overnight on LB agar supplemented with kanamycin (50 ug/ml) and ampicillin (100 ug/ml).

Cells were grown in auto-induction media for 18 hours at 37 C and then harvested, washed twice in PBS containing 1 mM MgCl2, and labeled with α-Flag (1:200, Sigma) for 1 hr at 4 C. The cells were then washed twice with PBS containing 1 mM MgCl2 and then labeled with R-PE conjugated α-mouse IgG (25 ug/mL, Thermo Fisher Scientific) for 1 hr at 4 C. following straining, cells were fixed in 2% formaldehyde for 20 minutes and further washed with PBS containing 1 mM MgCl2. Flow Cytometry was performed with a Becton Dickinson FACSCalibur and the results were analyzed using FLOWJO software. Mean fluorescence intensity (MFI) was calculated using at least three replicates was used to compare surface exposure the lipoprotein in strains either containing or lacking the putative SLAM (PM1515) and are shown in FIG. 11C and FIG. 11D. PM1514 could be detected on the surface of *E. coli* illustrating i) that SLAM can be used to identify SLPs and ii) that SLAM is required to translocate these SLPs to the surface of the cell—thus identifying a class of proteins call "SLAM-dependent surface lipoproteins". Antibodies were raised against purified PmSLP (PM1514) and the protein was shown to be on the surface of *Pasteurella multocida* via PK shaving assays.

Example 9: Identification of the Translocation Motif of SLAM-Dependent Surface Lipoproteins and the Role in SLAM Specificity Minimal domain and domain swap constructs used were pETDUET HpuA (SEQ ID NO: 1099), TbpB N-lobe (SEQ ID NO: 1095), TbpB C-lobe (SEQ ID NO: 1097), and TbpB N-lobe-HpuA (SEQ ID NO: 1101). The mature HpuA was amplified and inserted in frame with the signal peptide of TbpB and simultaneously replaced the rest of the TbpB gene in pETDUET TbpB to create pETDUET HpuA using restriction free cloning. The anchor peptide (amino acids 1-40), N-lobe of TbpB (amino acids 41-331) and the C-lobe of TbpB (amino acids 332-579) were parsed based on the *N. meningitidis* strain B16B6 TbpB structure (PDB ID 4QQ1). The N-lobe construct was cloned using inverse cloning to insert a stop codon between the N and C lobes of TbpB using pETDUET TbpB as template. The C-lobe construct of TbpB was cloned using restriction free cloning to insert and simultaneously replace the TbpB N-lobe in pETDUET TbpB N-lobe. The C-lobe was inserted in frame with the anchor peptide. The fusion construct pETDUET TbpB N-lobe-HpuA was cloned by inserting HpuA (amino acids 2-end) in frame with the N-lobe of pETDUET TbpB N-lobe by restriction free cloning. Poly-Ala mutations were created with FastCloning using pETDUET TbpB as template. Vectors containing either SLAM1 or SLAM2 were used.

Plasmids were transformed into *E. coli* C43 (DE3) cells and grown in auto-induction media for 18 hours at 37 C. Cells were harvested, washed twice in PBS containing 1 mM MgCl2, and labeled with either α-TbpB antibodies (1:200, rabbit sera) or biotinylated human transferrin (0.05 mg/ml, Sigma) for 1 hr at 4 C. The cells were then washed twice with PBS containing 1 mM MgCl2 and then labeled with R-FITC conjugated α-rabbit IgG (25 ug/ml, Thermo Fisher Scientific) for 1 hr at 4 C. Following staining, cells were fixed in 2% formaldehyde for 20 minutes and further washed with PBS containing 1 mM MgCl2. Flow Cytometry was performed with a Becton Dickinson FACSCalibur and the results were analyzed using FLOWJO software. Mean fluorescence intensity was calculated using at least three replicates and was used to compare surface exposure of a given SLP between different strains. The C-lobe of TbpB appears to be required for SLAM1 dependent translocation to the surface of *E. coli* (FIG. 12B), while the N-lobe does not appear to play a significant role. Additionally, the use of HpuA fused to the TbpB N-lobe shifts SLAM dependency from SLAM1 to SLAM2 (FIG. 12C-E).

Using the above methodology, four of the eight beta-barrel strands were probed for importance in surface display of surface lipoproteins. Mutation of two of the beta-barrel strands of *N. meningitidis* TbpB, strands B30 (SEQ ID NO: 1107) and B31 (SEQ ID NO: 1109), were shown to be required for surface expression of TbpB (FIG. 13C and FIG. 13D).

Multiple sequence alignments were performed on the last two strands of the eight-stranded barrel domain of the C-lobe from TbpB from *N. meningitidis, N. gonorrhoeae, M. catarrhalis, H. influenzae*, and *A. pleuropneumoniae*, the C-lobe of LbpB from *N. meningitidis* and *N. lactamica*, and from HpuA from *N. meningitidis, N. gonorrhoeae*, and *K. denitrificans*. Strand B30 was shown to have a conserved [L/M]GGx[F/I/V] sequence and stand B31 appears to have a conserved ϕx[A/T/V]FG[A/G] sequence, as shown in FIG. 13E.

Example 10: Identification of a Novel SLAM-Dependent Surface Lipoprotein in *Actinobacter baumannii*

*A. baumannii* is an opportunistic pathogen, and causes disease in intensive care patients, and those who are immunocompromised or have underlying disease (Camp, C. & Tatum, O. L. Lab. Med. 41, 649-657 (2010)). *A. baumannii* causes a variety of clinical manifestations such as pneumonia, sepsis and urinary tract infections. It has gained notoriety for causing soft tissue infections in combat zone hospitals. Multi-drug resistant *A. baumannii* poses a significant challenge to treating physicians and a threat to human health since *A. baumannii* is resistant to many of the antibiotics used in the clinic (Camp, C. & Tatum, O. L. Lab. Med. 41, 649-657 (2010)).

A SLAM-like protein (AbSLAM) was identified in a gene cluster in *A. baumannii* using iterative blast search with NmSLAM as the original query sequence (FIG. 14A) (SEQ ID NO: 1177 and 1178). Although this gene cluster was initially discovered by Antunes et al. while searching for genes involved in iron acquisition, the SLAM gene was misannotated as a hypothetical protein (Antunes, L. C. S., Imperi, F., Towner, K. J. & Visca, P. Res. Microbiol. 162, 279-284 (2011)). Adjacent to the SLAM gene is a gene encoding a lipoprotein of unknown function (AbSLP). This prediction is supported by the presence of a lipobox motif (LVAC) at the N-terminus of the protein.

We have demonstrated using flow cytometry that AbSLP can be exogenously expressed in *E. coli*, and localizes to the cell surface only when co-expressed with AbSLAM (FIG. 14B). Furthermore, the structure of AbSLP was solved by X-ray crystallography (FIG. 14C). AbSLP is comprised of an N-terminal β-handle consisting of 8 antiparallel ß-strands and a C-terminal 8 stranded ß-barrel. The structure shows that AbSLP is a heme binding protein with high structural similarity to the structures of known SLAM-dependent SLPs (TbpB, LbpB, HpuA) (FIG. 1B-C and FIG. 2). Expressing AbSLP with its SLAM leads to surface display of AbSLP in *E. coli* (FIG. 14B). Antibodies to AbSLP were raised and illustrate that AbSLP is located on the surface of *A. baumannii* (LAC4) by Proteinase K shaving (FIG. 14D).

The discovery of the novel SLP AbSLP by the presence of an adjacent SLAM gene illustrates the utility of SLAM to identify potential vaccine antigen SLPs that are located adjacent to the SLAM gene.

While the present disclosure has been described with reference to what are presently considered to be the preferred examples, it is to be understood that the disclosure is not limited to the disclosed examples. To the contrary, the disclosure is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

---

SEQUENCE LISTING

The patent contains a lengthy sequence listing. A copy of the sequence listing is available in electronic form from the USPTO web site (https://seqdata.uspto.gov/?pageRequest=docDetail&DocID=US12296000B2). An electronic copy of the sequence listing will also be available from the USPTO upon request and payment of the fee set forth in 37 CFR 1.19(b)(3).

---

The invention claimed is:

1. A method of preparing a vaccine comprising:

(a) selecting a host cell capable of producing an immunogen;

(b) providing a chimeric polynucleotide comprising as operably linked components:

(i) a polynucleotide capable of controlling expression in the host cell; and (ii) a polynucleotide encoding a Surface Lipoprotein Assembly Modulator (SLAM) polypeptide, wherein the polynucleotide comprises a polynucleotide sequence selected from the group consisting of SEQ.ID NO: 5; SEQ.ID NO: 199; SEQ. ID NO: 273; SEQ. ID NO: 385; SEQ. ID NO: 387; SEQ.ID NO: 1087; SEQ.ID NO: 1111; SEQ.ID NO: 1181; and SEQ.ID NO: 1183, or a polynucleotide sequence that encodes a polypeptide that is at least 90% identical to a polypeptide encoded by any of the foregoing polynucleotides;
(c) introducing the chimeric nucleic acid sequence in the host cell and growing the host cell to produce the SLAM polypeptide and the immunogen;

(d) attenuating the host cell to prepare an attenuated host cell; and (e) preparing a vaccine formulation comprising the immunogen using from the attenuated host cell, wherein upon administration of the vaccine formulation to a subject, the immunogen stimulates the immune system of the subject to generate a cellular or humoral antibody immunogen-specific response.

2. A method according to claim 1, wherein the host cell is a microbial cell.

3. A method according to claim 2, wherein the microbial cell is a pathogenic microbial cell.

4. A method according to claim 2, wherein the microbial cell is selected from a *Neisseria* cell, a *Klebsiella* cell, a *Moraxella* cell, an *Actinobacillus* cell, a *Haemophilus* cell, a *Pasteurella* cell, an *Acinetobacter* cell, or a *Vibrio* cell.

5. A method according to claim 2, wherein the microbial cell is selected from a *Neisseria meningitidis* cell, a *Neisseria gonorrhoeae* cell, a *Neisseria* lactamica cell, *Neisseria cincera* cell, a *Klebsiella denitrificans* cell, a *Moraxella catarrhalis* cell, a *Moraxella haemolytica* cell, an *Actinobacillus pleuropneumoniae* cell, a *Haemophilus somni* cell, a *Haemophilus influenzae* cell, a *Pasteurella multocida* cell, an *Acinetobacter baumannii* cell, or a *Vibrio cholera* cell.

6. The method according to claim 1 further comprising:

in step (b):

providing a second chimeric polynucleotide comprising as operably linked components:

(i) a polynucleotide capable of controlling expression in the host cell; and (ii) a polynucleotide encoding an immunogen; and in step (c):

introducing the second chimeric polynucleotide in the host cell and growing the host cell to produce the SLAM polypeptide and the immunogen.

7. The method according to claim 2, wherein the immunogen is naturally displayed on the exterior surface of a pathogenic microorganism.

8. The method according to claim 7, wherein the pathogenic microorganism is selected from the group consisting of *Neisseria meningitidis, Neisseria gonorrhoeae, Neisseria lactamica, Neisseria cincera, Klebsiella denitrificans, Moraxella catarrhalis, Moraxella haemolytica, Actinobacillus pleuropneumoniae, Haemophilus somni, Haemophilus influenzae, Pasteurella multocida, Acinetobacter baumannii* or *Vibrio cholera.*

9. The method according to claim 1, wherein the immunogen is a surface lipoprotein (SLP).

10. The method according to claim 9, wherein the SLP is selected from a transferrin binding protein B (TbpB), a hemoglobin-haptoglobin binding protein A (HpuA), a Factor H binding protein (fHbp), and a lactoferrin binding protein (LbpB).

11. The method according to claim 1, wherein the SLAM polypeptide is not naturally present in the host cell.

12. The method according to claim 1, wherein the target polypeptide is naturally present in the host cell.

13. The method according to claim 1, wherein the host cells are attenuated by heat-killing the host cells.

14. The method according to claim 1, wherein the host cells are attenuated by heat-killing the host cells to obtain heat-killed host cells, and wherein vaccine formulation is prepared by including the heat-killed host cells in the vaccine formulation.

15. The method according to claim 1, wherein the host cells are attenuated by heat-killing the host cells to obtain heat-killed host cells, and wherein the heat-killed host cells are used to prepare outer membrane vesicles, and wherein the vaccine formulation is prepared by including the outer membrane vesicles in the vaccine formulation.

16. A vaccine preparation made using the attenuated host cells obtained according to claim 1.

* * * * *